(12) United States Patent
Baumann et al.

(10) Patent No.: US 9,266,906 B2
(45) Date of Patent: Feb. 23, 2016

(54) COPPER(I) COMPLEXES FOR OPTOELECTRONIC DEVICES

(75) Inventors: Thomas Baumann, Karlsruhe (DE); Tobias Grab, Karlsruhe (DE); Larissa Bergmann, Karlsruhe (DE)

(73) Assignee: CYNORA GMBH, Eggenstein-Leopoldshafen (DE)

( * ) Notice: Subject to any disclaimer, the term of this patent is extended or adjusted under 35 U.S.C. 154(b) by 16 days.

(21) Appl. No.: 14/131,631

(22) PCT Filed: Jul. 9, 2012

(86) PCT No.: PCT/EP2012/063444
§ 371 (c)(1),
(2), (4) Date: Mar. 6, 2014

(87) PCT Pub. No.: WO2013/007707
PCT Pub. Date: Jan. 17, 2013

(65) Prior Publication Data

US 2014/0235006 A1    Aug. 21, 2014

(30) Foreign Application Priority Data

Jul. 8, 2011 (EP) .................................. 11173371
Aug. 5, 2011 (EP) .................................. 11176760
Aug. 26, 2011 (EP) .................................. 11179112

(51) Int. Cl.
*C07F 1/08*       (2006.01)
*H01L 51/56*      (2006.01)
*C07F 9/50*       (2006.01)
*C09K 11/06*      (2006.01)
(Continued)

(52) U.S. Cl.
CPC . *C07F 1/08* (2013.01); *C07F 1/005* (2013.01); *C07F 9/5045* (2013.01); *C09K 11/06* (2013.01); *H01L 51/0091* (2013.01); *H01L 51/56* (2013.01); *C09K 2211/1007* (2013.01); *C09K 2211/1029* (2013.01); *C09K 2211/1044* (2013.01); *C09K 2211/1048* (2013.01); *C09K 2211/1051* (2013.01); *C09K 2211/1059* (2013.01); *C09K 2211/188* (2013.01);
(Continued)

(58) Field of Classification Search
CPC ..... C07F 1/08; C07F 9/5045; H01L 51/0091; C09K 11/06
See application file for complete search history.

(56) References Cited

FOREIGN PATENT DOCUMENTS

WO          2010031485 A1      3/2010

OTHER PUBLICATIONS

International Search Report and Written Opinion of International Searching Authority for PCT/EP2012/063444 dated Oct. 31, 2012.

*Primary Examiner* — Joseph Kosack
(74) *Attorney, Agent, or Firm* — Ryan, Mason & Lewis, LLP

(57) ABSTRACT

Copper(I) complexes for the emission of light with a structure according to formula A:

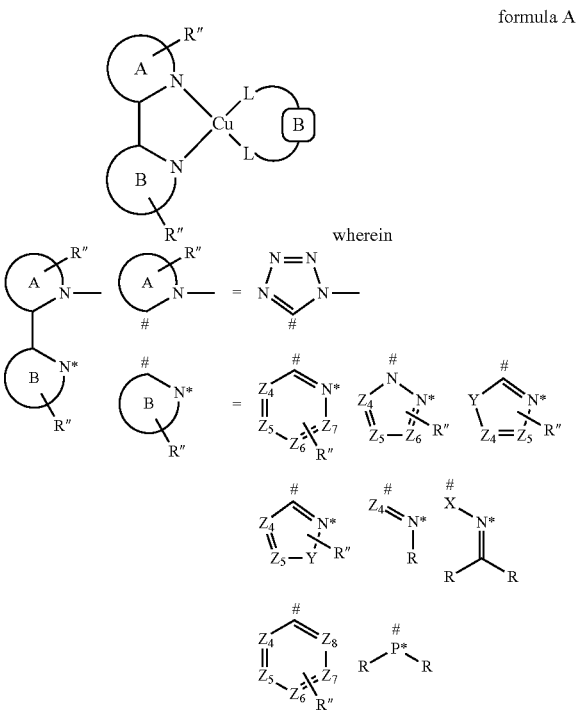

wherein:
  M is Cu(I);
  L-B-L: a neutral, bidentate ligand,
  Z4-Z7: includes N or the fragment CR, with R=organic group, selected from the group consisting of: hydrogen, halogen or deuterium or groups which are bound via oxygen (—OR'''), nitrogen (—NR'''$_2$), or phosphorous atoms (PR'''$_2$) as well as alkyl, aryl, heteroaryl, alkenyl, alkinyl, trialkylsilyl and triarylsilyl groups or substituted alkyl, aryl, heteroaryl and alkenyl groups with substituents such as halogens or deuterium or lower alkyl groups;
  X is either CR'''$_2$ or NR''';
  Y is either O, S or NR''';
  Z8 includes the fragment CR', with R'=O*R''', N*R'''$_2$ or P*R'''$_2$, wherein the bond to the Cu atom is carried out via these groups;
  R'' is a sterically demanding substituent, which inhibits a change in geometry in direction to planarization of the complex in excited state,
  R'''=organic group which is selected from the group consisting of: hydrogen, halogen or deuterium, as well as alkyl, aryl, heteroaryl, alkenyl, alkinyl groups or substituted alkyl, aryl, heteroaryl and alkenyl groups with substituents such as halogens or deuterium, alkyl groups, and further generally known donor and acceptor groups
  * indicates the atom which receives the complex bond; and
  # indicates the atom which mediates the bond with the second chemical unit.

20 Claims, 10 Drawing Sheets

(51) Int. Cl.
  *H01L 51/00* (2006.01)
  *C07F 1/00* (2006.01)
  *H01L 51/50* (2006.01)

(52) U.S. Cl.
  CPC ......... *H01L51/5016* (2013.01); *H01L 2251/10* (2013.01); *Y02B 20/181* (2013.01); *Y02E 10/549* (2013.01)

Figure 3. Crystal structure of 2c
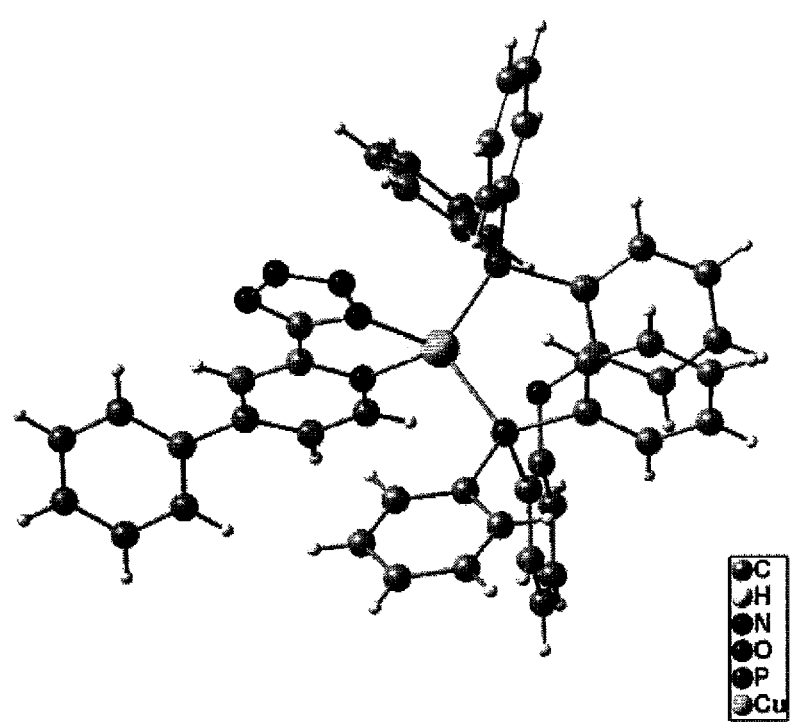

Figure 4. Crystal structure of 2d
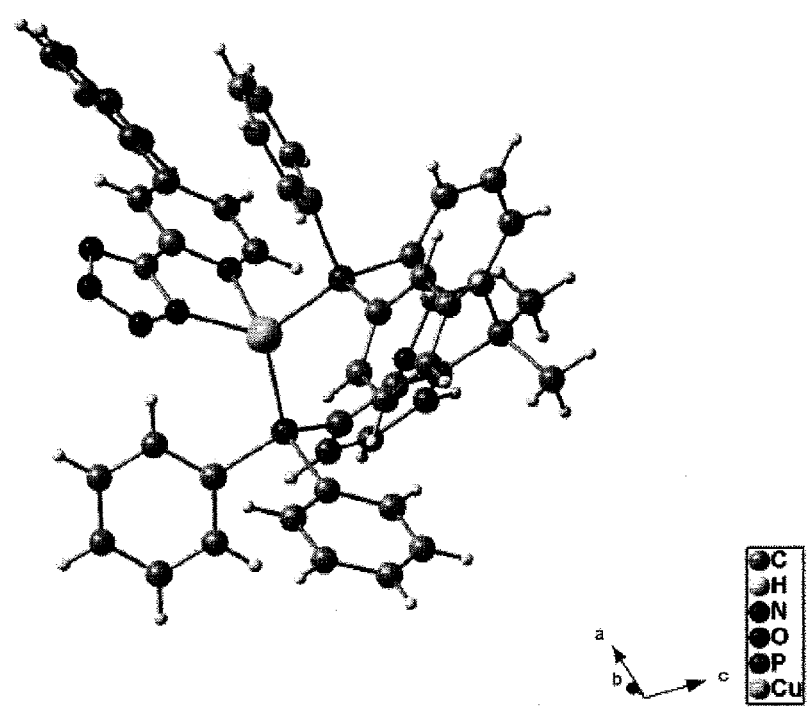

Figure 5. Crystal structure of 8a
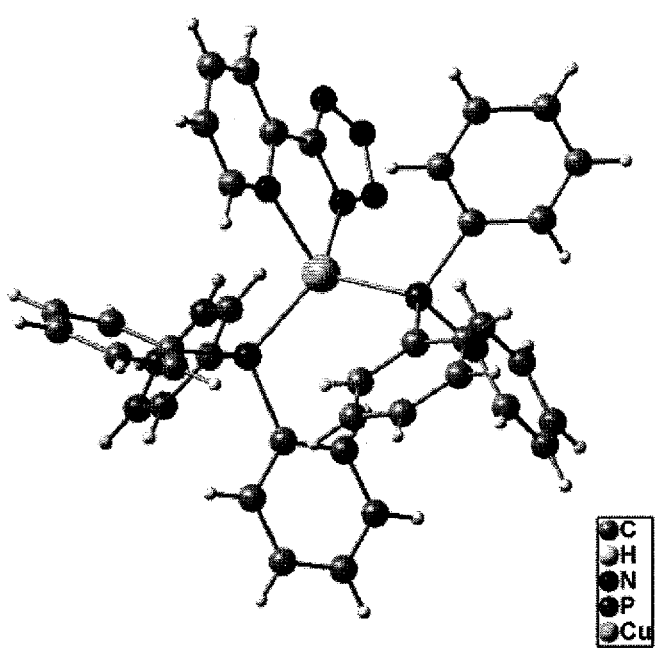

Figure 6. Emission spectrum of 2c
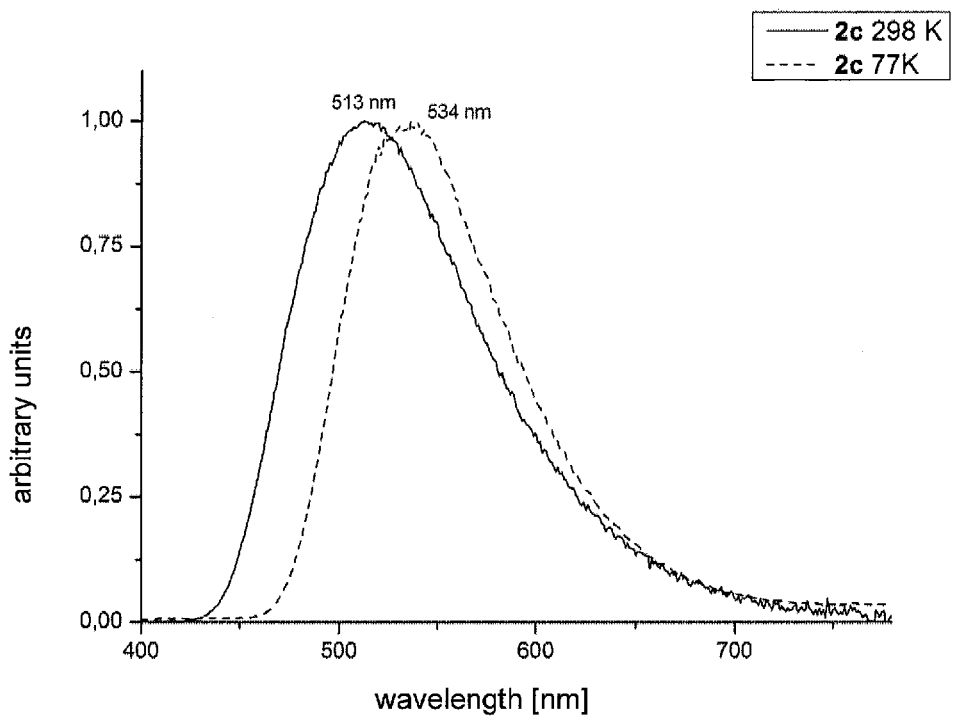
Figure 7. Emission spectrum of 2d
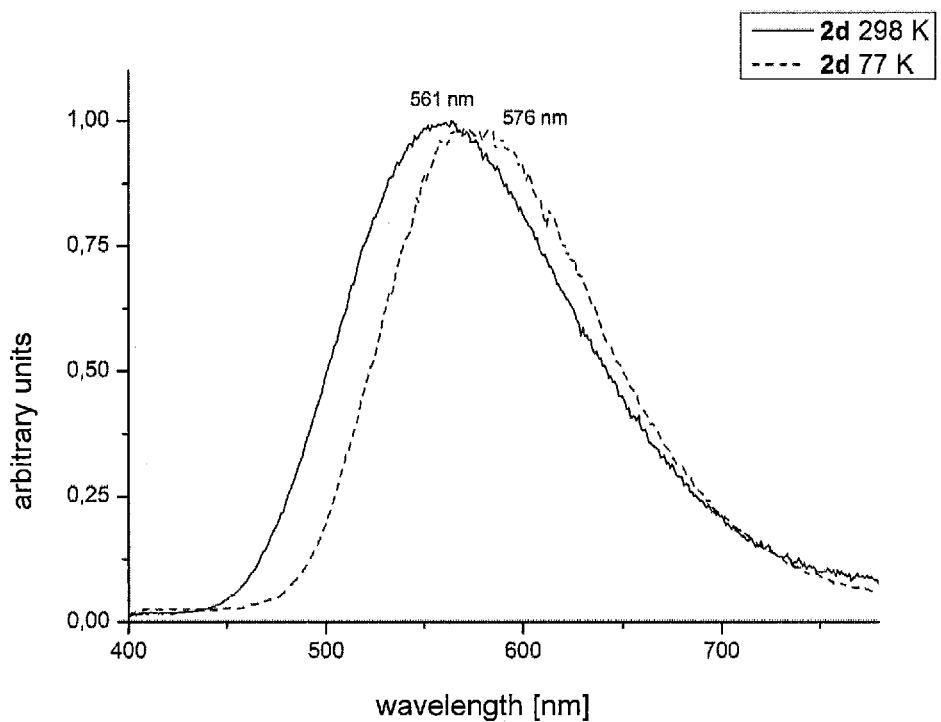

Figure 8. Emission spectrum of 2e
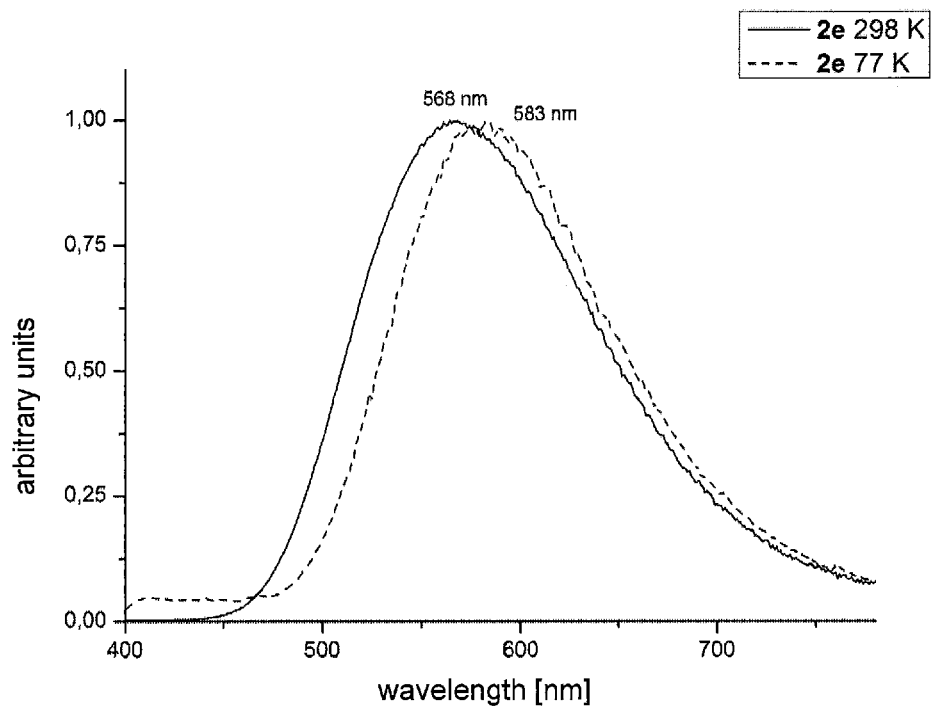
Figure 9. Emission spectrum of 4c
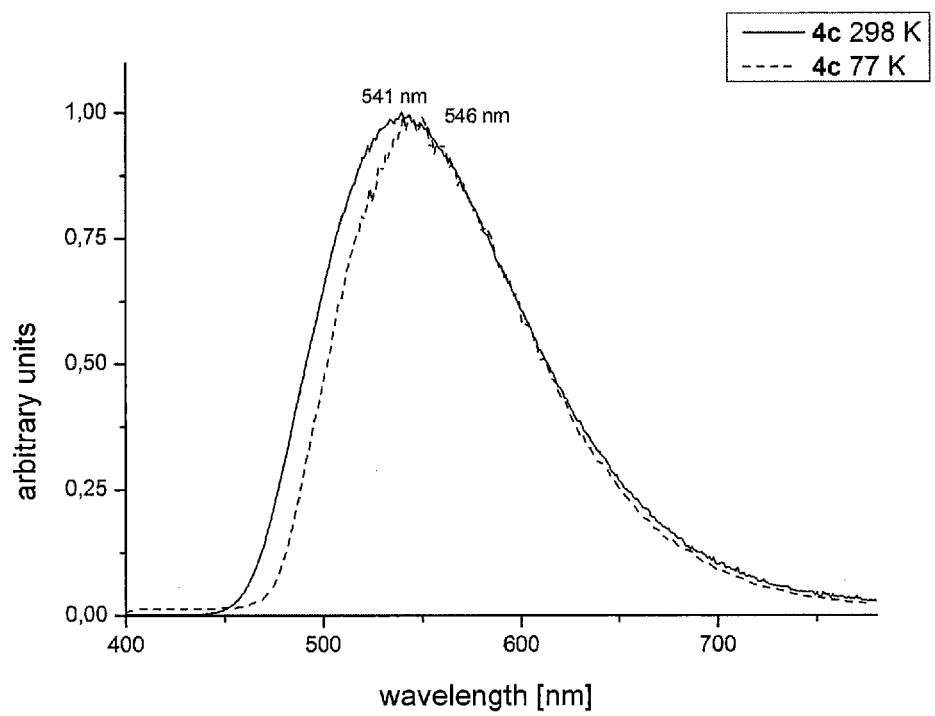

Figure 10. Emission spectrum of 6c
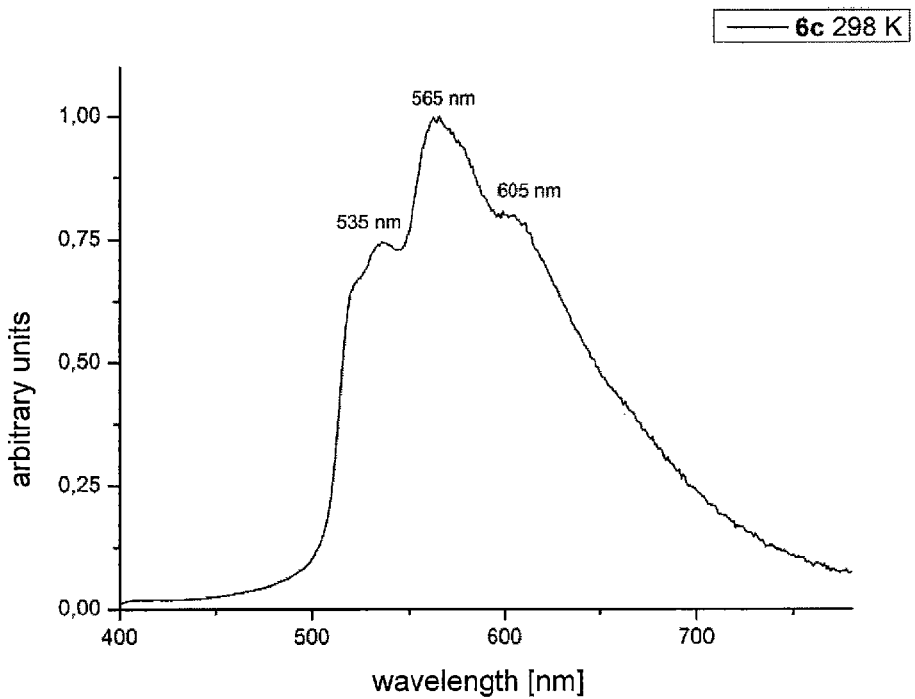
Figure 11. Emission spectrum of 6e
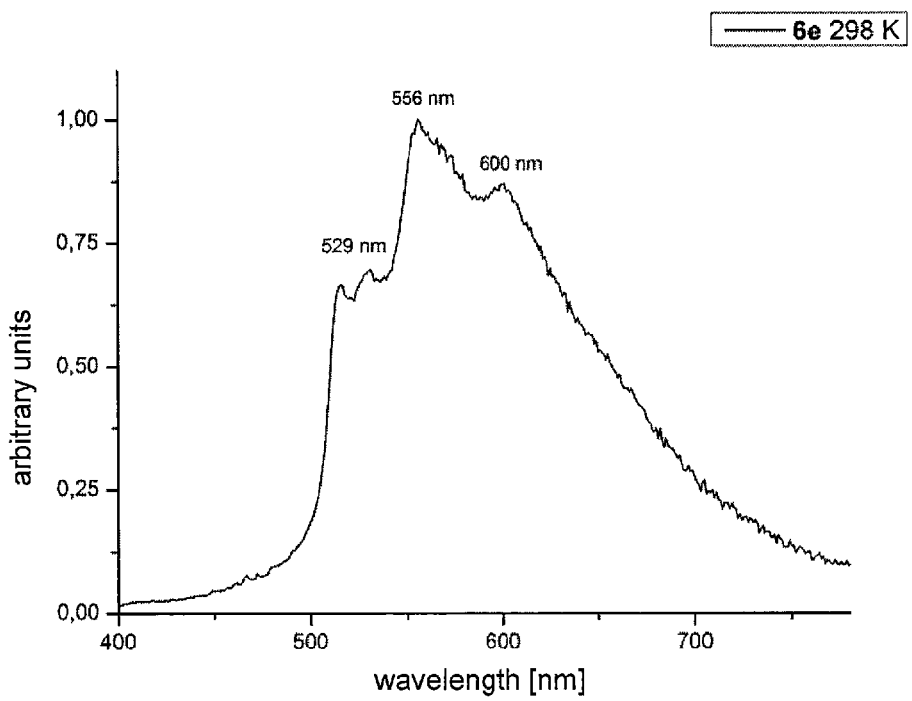

Figure 12. Emission spectrum of 8c
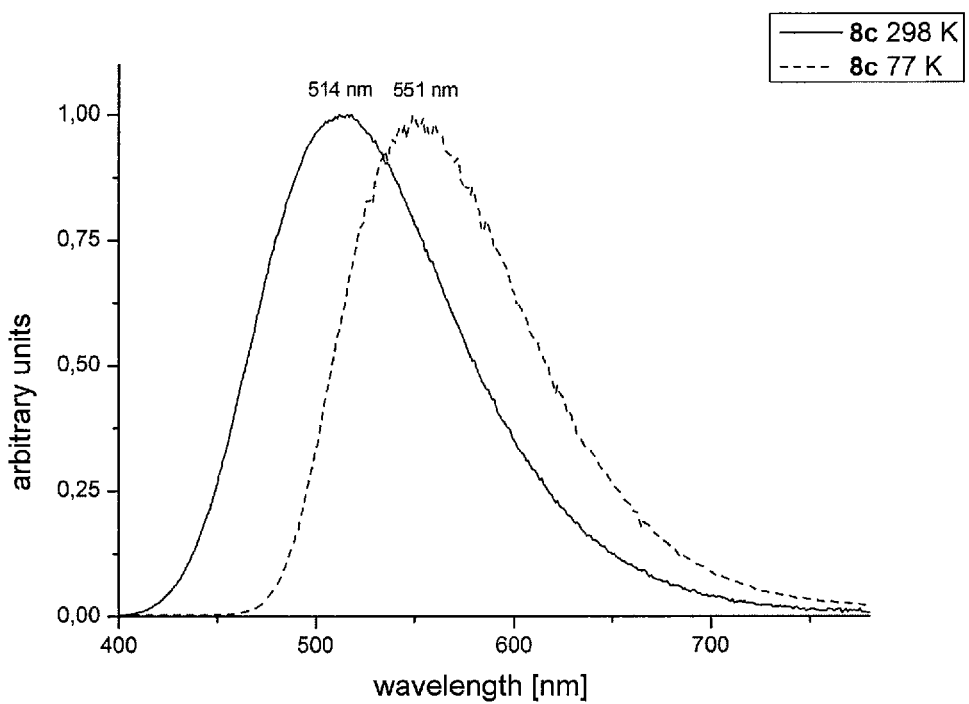
Figure 13. Emission spectrum of 8d
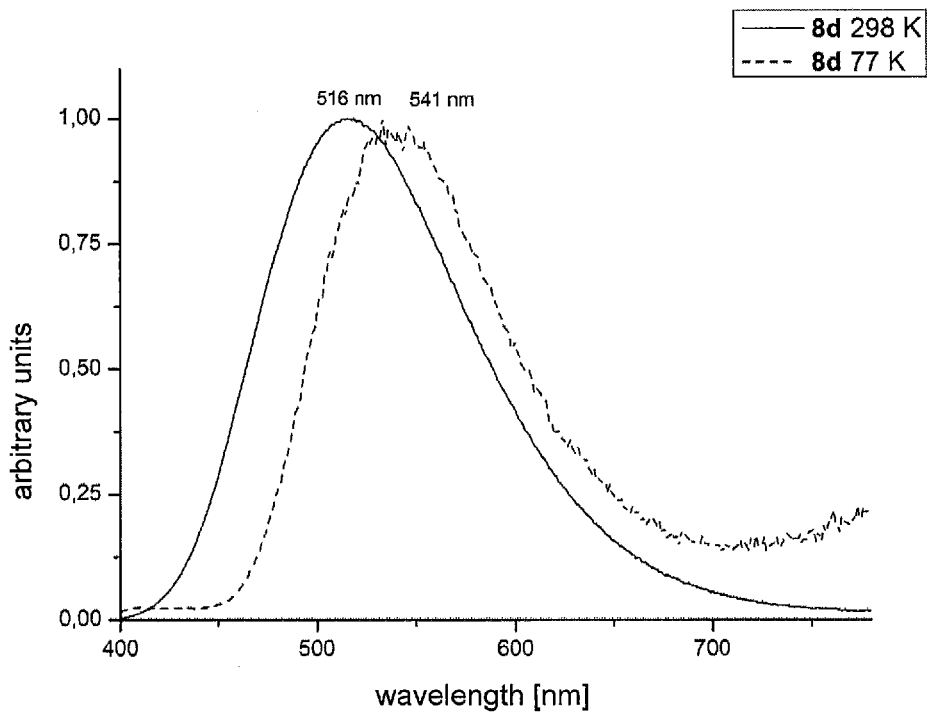

Figure 14. Emission spectrum of 8e
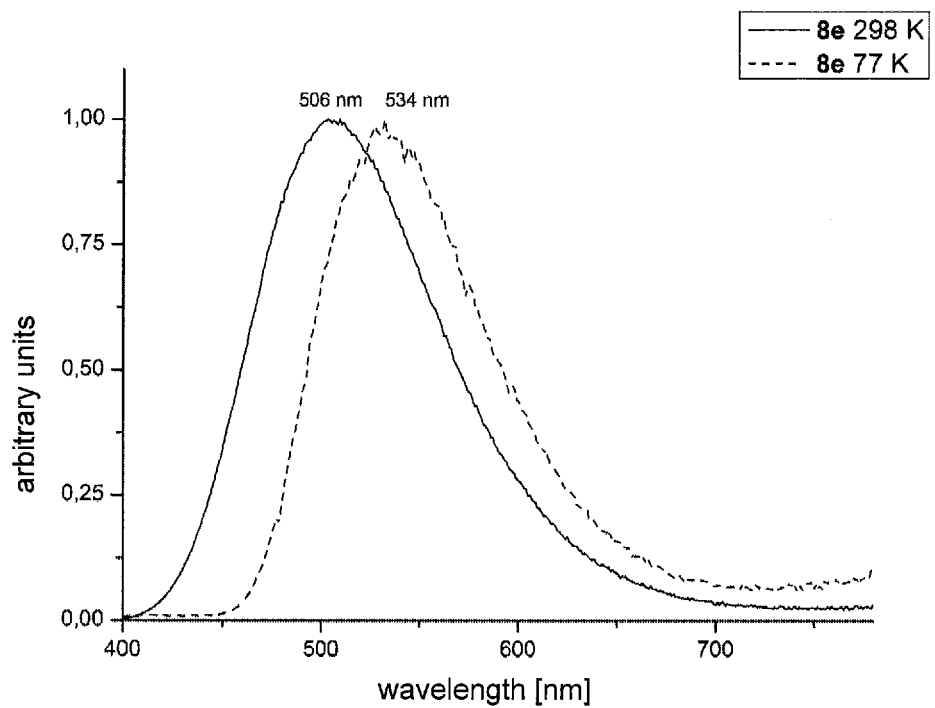

COPPER(I) COMPLEXES FOR OPTOELECTRONIC DEVICES

FIELD OF INVENTION

The present invention relates to the use of soluble copper(I) complexes (Cu(I)-complexes) as emitters in OLEDs (organic light emitting diodes) and in other optoelectronic devices.

BACKGROUND OF THE INVENTION

In principle, OLEDs are outstandingly suitable for the production of large-area illumination and display applications but can be found only in devices of small format at the moment due to extensive production methods. OLEDs are generally implemented in layer structures. For better understanding, FIG. 1 shows a basic structure of an OLED. Owing to the application of external voltage to a transparent indium tin oxide (ITO) anode and a thin metal cathode, the anode injects positive holes, and the cathode negative electrons. These differently charged charge carriers pass through intermediate layers, to which also hole or electron blocking layers not shown here may belong, into the emission layer. The oppositely charged charge carriers meet therein at or close to doped emitter molecules, and recombine. The emitter molecules are generally incorporated into matrices molecules or polymer matrices (in, for example, 2 to 10% by weight), the matrix materials being selected so as also to enable hole and electron transport. The recombination gives rise to excitons (=excited states), which transfer their excess energy to the respective electroluminescent compound. This electroluminescent compound can then pass into a particular electronic excited state, which is then converted very substantially and with substantial avoidance of radiationless deactivation processes to the corresponding ground state by emission of light.

With a few exceptions, the electronic excited state, which can also be formed by energy transfer from a suitable precursor exciton, is either a singlet or triplet state, consisting of three sub-states. Since the two states are generally occupied in a ratio of 1:3 on the basis of spin statistics, the result is that the emission from the singlet state, which is referred to as fluorescence, leads to maximum emission of only 25% of the excitons produced. In contrast, triplet emission, which is referred to as phosphorescence, exploits and converts all excitons and emits them as light (triplet harvesting) such that the internal quantum yield in this case can reach the value of 100%, provided that the also excited singlet state, which is above the triplet state in terms of energy, relaxes fully to the triplet state (intersystem crossing, ISC), and radiationless competing processes remain insignificant. Thus, triplet emitters, according to the current state of the art, are more efficient electroluminophores and are better suitable for ensuring a high light yield in an organic light emitting diode.

The triplet emitters suitable for triplet harvesting used are generally transition metal complexes in which the metal is selected from the third period of the transition metals. This predominantly involves very expensive noble metals such as iridium, platinum or else gold (see also H. Yersin, Top. Curr. Chem. 2004, 241, 1 and M. A. Baldo, D. F. O'Brien, M. E. Thompson, S. R. Forrest, Phys. Rev. B 1999, 60, 14422). The prime reason for this is the high spin-orbit-coupling (SOC) of noble metal central ions (SOC constants Ir(III): ≈4000 cm$^{-1}$; Pt(II): ≈4500 cm$^{-1}$; Au(I): ≈5100 cm-1; Ref.: S. L. Murov, J. Carmicheal, G. L. Hug, Handbook of Photochemistry, 2nd Edition, Marcel Dekker, New York 1993, p. 338 ff). Due to this quantum mechanical characteristic, the triplet-singlet transition, which is without SOC strictly forbidden for optical transitions, is allowed and an emission lifetime of a few μs, needed for OLED applications is achieved.

Economically, it would be highly advantageous if these expensive noble metals could be replaced with less expensive metals. Moreover, a large number of OLED emitter materials known to date are ecologically problematic, so that the use of less toxic materials would be desirable.

BRIEF DESCRIPTION OF THE DRAWINGS

Exemplary embodiments of the present invention will be described below in more detail, with reference to the accompanying drawings, of which:

FIGS. 3-5 show Oak Ridge Thermal Ellipsoid Plot (ORTEP) depictions of different Cu(N∩L)(L-B-L) complexes according to embodiments of the present invention.

FIG. 3 shows the crystal structure of complex 2c.
FIG. 4 shows the crystal structure of complex 2d.
FIG. 5 shows the crystal structure of complex 8a.
FIGS. 6-14 shows the emission spectra of different Cu(N∩L)(L-B-L) complexes according to embodiments of the present invention.
FIG. 6 shows the emission spectrum of complex 2c.
FIG. 7 shows the emission spectrum of complex 2d.
FIG. 8 shows the emission spectrum of complex 2e.
FIG. 9 shows the emission spectrum of complex 4c.
FIG. 10 shows the emission spectrum of complex 6c.
FIG. 11 shows the emission spectrum of complex 6e.
FIG. 12 shows the emission spectrum of complex 8c.
FIG. 13 shows the emission spectrum of complex 8d.
FIG. 14 shows the emission spectrum of complex 8e.

DETAILED DESCRIPTION OF EXEMPLARY EMBODIMENTS OF THE INVENTION

Figure 1:
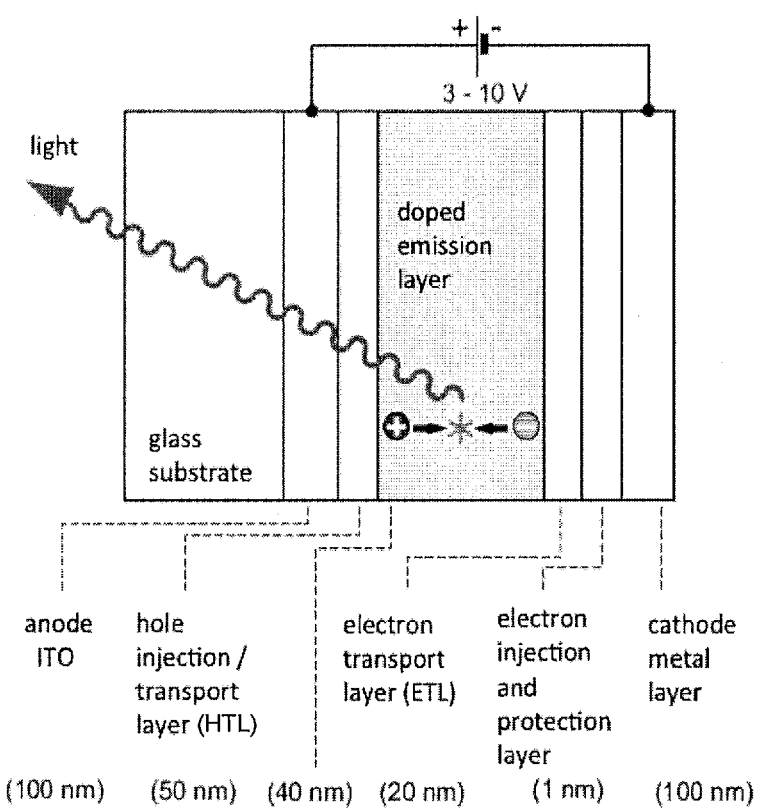
FIG. 1 shows the basic structure of an OLED. The figure is not drawn to scale.
Figure 2:
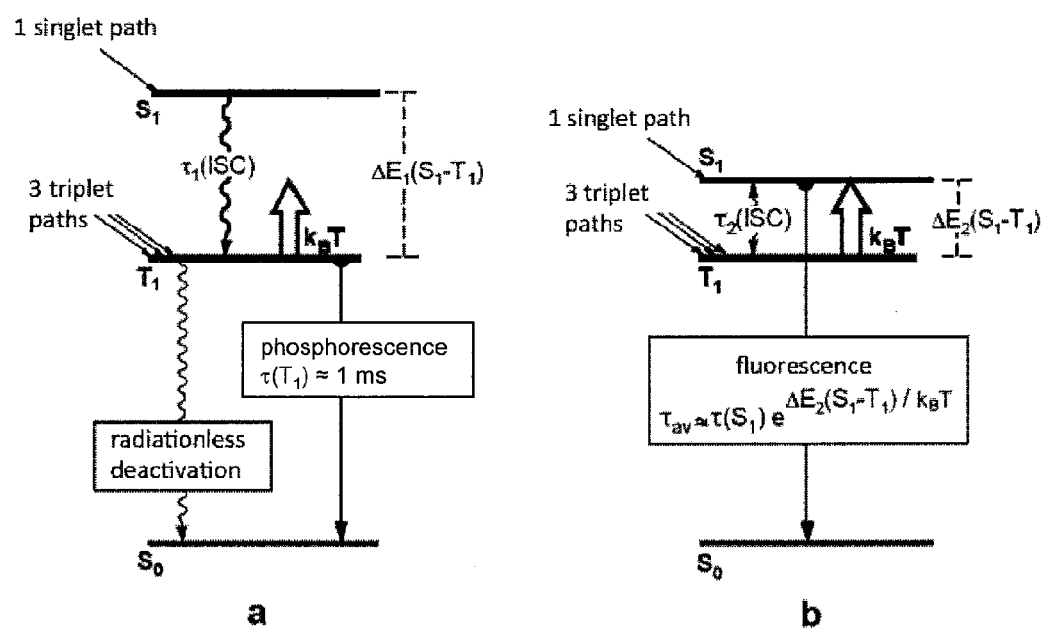
FIG. 2a shows an illustration of the electro luminescence behavior for transition metal complexes with a spin orbit coupling that is small or has a small effect (e.g., metal complexes of the first period of the transition metals) and FIG. 2b for Cu(I)-complexes selected according to embodiments of the .resent invention. The value of $\tau(T_1)$ in FIG. 2a represents an example.

Exemplary embodiments of the invention will now be discussed in further detail. This invention may, however, be embodied in many different forms and should not be construed as limited to the embodiments set forth herein.

The invention refers to the creation and provision of novel Cu(I) compounds with improved characteristics. Particularly, the Cu(I) compounds comprise the following characteristics:
  relatively short emission lifetimes of only a few μs,
  high emission quantum yields of greater than 40%,
  prevention of unwanted changes of geometry to a large extent, and/or
  solubility in different solvents that satisfy the technological requirements.
Organic solvents according to the invention are
alkanes, also halogenated alkanes such as pentane, hexane, heptane, including branched alkanes, dichloromethane, chloroform, 1,2-dichlorethane, 1,1,1-trichlorethane, carbon tetrachloride, perchloroethylene, aromatic hydrocarbons, also halogenated: benzene, toluene, mesitylene, chlorobenzene 1,2-dichlorobenzene, ethers: tetrahydrofuran, diethyl ether, phenetol, ketones: acetone, methyl ethyl ketone, propiophenone, as well as: acetonitrile, nitromethane, dimethyl sulfoxide, dimethyl formamide, methanol, ethanol and ethyl acetate.

In certain embodiments of the invention, the copper(I) complex is well-soluble in particular in at least one of the following solvents: polar hydrocarbons like, for example, dichlormethane, chloroform, 1,2-dichlorethane, 1,1,1-trichlorethane, perchloroethylene, toluene, mesitylene, chlorbenzene, 1,2-dichlorobenzene, tetrahydrofuran, diethyl ether, phenetol, acetone, methyl ethyl ketone, propiophenone, nitromethane, dimethyl sulfoxide, dimethyl formamide, methanol, and ethanol.

Stabilization of the Molecular Structure

Quadrupel-coordinated complexes have an almost tetrahedral coordination of the metal atom in the electronic ground state. In case of excitation into an electronic excited state with pronounced metal-to-ligand charge-transfer character and the associated formal oxidation of the metal atom to Cu(II), considerably changes in the geometry of the complex towards a square-planar coordination can occur, which therefore can be referred to as "planarization" of the complex molecule. This process provides for a very effective mechanism for quenching luminescence.

In copper(I) complexes according to the invention, this quenching mechanism is prevented or strongly reduced by the presence of sterically demanding substituents at the singly negatively charged ligand N∩L (particularly in ortho position to the coordination points) by a hindrance of change of geometry around the Cu atom. At the same time, such substitutions help to prevent nucleophilic reactions with the Cu center (with solvents, contaminants, easily coordinating matrix materials). Just one methyl group leads to an observable "stiffening" of the resulting Cu complexes. A sterically demanding substituent therefore is, besides methyl, particularly an alkyl group —$(CH_2)_n$—$CH_3$ (n=0-20) (also branched), an aryl group with 6-20 carbon atoms (e.g. -Ph), alkoxy group —O—$(CH_2)_n$—$CH_3$ (n=0-20), an aryloxy group (e.g. —OPh) or a silane group (e.g. —$SiMe_3$). The alkyl and aryl groups can also be substituted (e.g. with halogens, deuterium, alkoxy or silane groups, etc.) or lead to annulated ring systems.

Chemical Lead Structure

The emitter according to the invention is an emitter comprising a structure of formula 1:

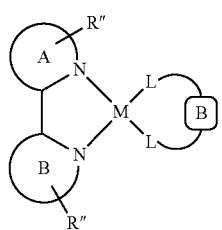

Formula 1 wherein

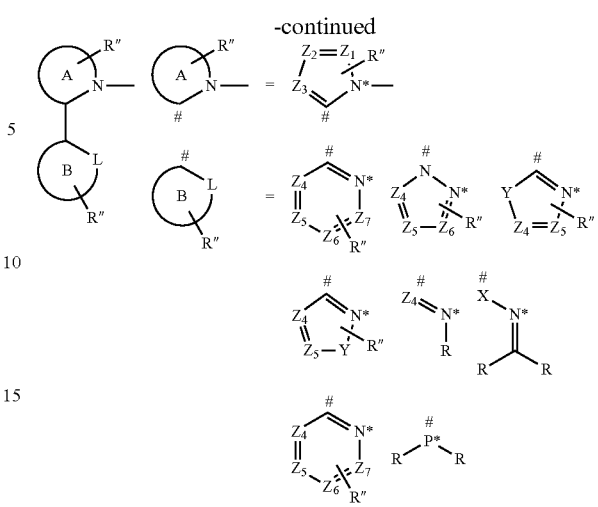

With:

M is Cu(I);

L-B-L is a neutral, bidentate ligand. Preferably, L is a phosphinyl or arsinyl group E*(R1)(R2), with E=P or As; R1, R2 can each independently from each other be hydrogen, halogen or deuterium or substituents which are bound via oxygen (—OR'''), nitrogen (—NR'''$_2$) or silicon atoms (—SiR'''$_3$) as well as alkyl- (also branched or cyclic), aryl, heteroaryl, alkenyl, alkinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and $CF_3$-groups, which is bound to another group L via a bridge B and thereby forms a bidentate ligand, wherein the bridge B is a alkylene or arylene group or a combination of both, or —O—, —NR'''— oder —SiR'''$_2$—. The groups R1-R2 can also lead to annulated ring systems;

Z1-Z7: consists of N or the fragment CR, with R=organic group, selected from the group consisting of: hydrogen, halogen or deuterium or groups which are bound via oxygen (—OR'''), nitrogen (—NR'''$_2$), silicon (—SiR'''$_3$) or phosphorous atoms (PR'''$_2$) as well as alkyl- (also branched or cyclic), aryl, heteroaryl, alkenyl, alkinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and $CF_3$-groups;

X is either CR'''$_2$ or NR''';

Y is either O, S or NR''';

Z8 consists of the fragment CR', with R'=O*R''', N*R'''$_2$ or P*R'''$_2$, wherein the bond to the Cu atom is formed via these groups;

R'' is a sterically demanding substituent, preferably in ortho position respective to the coordination point, which prevents a change in geometry in the direction of a planarization of the complex in an excited state. A sterically demanding substituent is in particular an alkyl group —$(CH_2)_n$—$CH_3$ (n=0-20) (also branched), an aryl group with 6-20 carbon atoms (e.g. -Ph), alkoxy group —O—$(CH_2)_n$—$CH_3$ (n=0-20), an aryloxy group (e.g. —OPh) or a silane group (e.g —$SiMe_3$). The alkyl and aryl groups can also be substituted (e.g. with halogens, deuterium, alkoxy or silane groups etc.) or lead to annulated ring systems. Even though there are two groups R″ shown in formula A, a complex according to the invention can, in one embodiment of the invention, also comprise no or only one group R″.

R′″=organic group which is selected from the group consisting of: hydrogen, halogen or deuterium, as well as alkyl- (also branched or cyclic), aryl, heteroaryl, alkenyl, alkinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and $CF_3$-groups.

In addition, the copper(I) complex can optionally comprise a function group (FG). This is a further substituent that inserts an additional function into the complex, which the complex would otherwise not comprise. The function groups FG are either attached directly or via suitable bridges (see below) to the N∩L-substituents.

It can either be a group with the characteristics of an electron conductor.

It can be a group comprising the characteristics of a hole conductor.

It can be a group that affects the solubility of the complex.

"*" indicates the atom which forms the complex bond.

"#" indicates the atom which is bound to the second chemical unit.

A preferred embodiment of the invention refers to the stable emitters of formula A which are characterized by an outstanding stability:

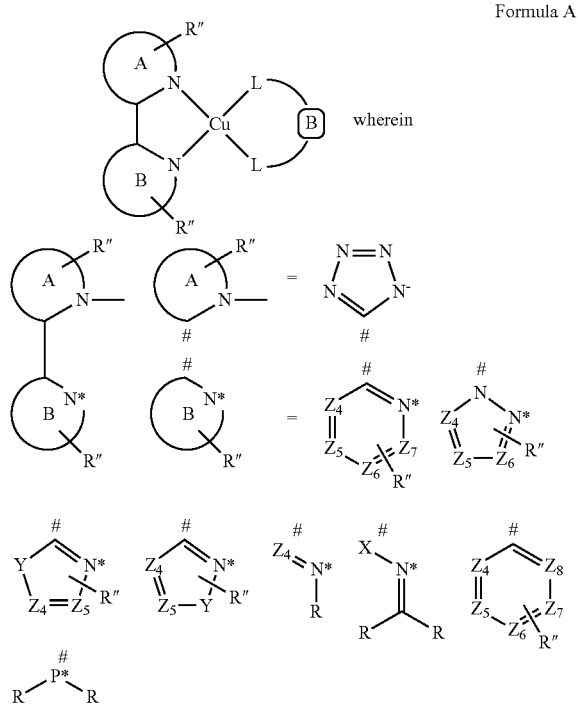

Formula A wherein:

M is Cu(I);

L-B-L: a neutral, bidentate ligand, preferably a phosphinyl or arsinyl group E*(R1)(R2), with E=P or As; R1, R2 can each independently from each other be hydrogen, halogen or deuterium or substituents which are bound via oxygen (—OR′″), nitrogen (—NR′″$_2$) or silicon atoms (—SiR′″$_3$) as well as alkyl- (also branched or cyclic), aryl, heteroaryl, alkenyl, alkinyl groups or substituted alkyl (also branched or cyclic), aryl, heteroaryl and alkenyl groups with substituents such as halogens or deuterium, alkyl groups (also branched or cyclic), and further generally known donor and acceptor groups such as for example amines, carboxylates and their esters, and $CF_3$-groups, which is bound to another group L via a bridge B and thereby forms a bidentate ligand, wherein the bridge B is an alkylene or arylene group or a combination of both, or —O—, —NR′″— or —SiR′″$_2$—, wherein the groups R1-R2 optionally form annulated ring systems;

Z4-Z7: consists of N or the fragment CR, with R=organic group, selected from the group consisting of: hydrogen, halogen or deuterium or groups which are bound via oxygen (—OR′″), nitrogen (—NR′″$_2$), silicon (—SiR′″$_3$) or phosphorous atoms (PR′″$_2$) as well as alkyl- (also branched or cyclic), aryl, heteroaryl, alkenyl, alkinyl groups or substituted alkyl (also branched or cyclic), aryl, heteroaryl and alkenyl groups with substituents such as halogens or deuterium, alkyl groups (also branched or cyclic), and further generally known donor and acceptor groups such as for example amines, carboxylates and their esters, and $CF_3$-groups.

X is either CR′″$_2$ or NR′″;

Y is either O, S or NR′″;

Z8 consists of the fragment CR′; with R′=OR′″, NR′″$_2$ or PR′″$_2$, wherein the bond to the Cu atom is then carried out via these groups;

R″ is a sterically demanding substituent, preferably in position ortho to the coordination point, which prevents a change in geometry in direction to planarization of the complex in excited state, preferably an alkyl group —(CH$_2$)$_n$—CH$_3$ (n=0-20) (also branched), an aryl group with 6-20 carbon atoms (e.g. -Ph), alkoxy group —O—(CH$_2$)$_n$—CH$_3$ (n=0-20), an aryloxy group (e.g. —OPh) or a silane group (e.g —SiMe$_3$), wherein the alkyl and aryl groups can also be substituted (e.g. with halogens, deuterium, alkoxy or silane groups) and optionally lead to annulated ring systems, wherein formula A comprises no, one or two groups R″;

R′″=organic group which is selected from the group consisting of: hydrogen, halogen or deuterium, as well as alkyl- (also branched or cyclic), aryl, heteroaryl, alkenyl, alkinyl groups or substituted alkyl (also branched or cyclic), aryl, heteroaryl and alkenyl groups with substituents such as halogens or deuterium, alkyl groups (also branched or cyclic), and further generally known donor and acceptor groups such as for example amines, carboxylates and their esters, and $CF_3$-groups;

optionally the copper(I) complex can comprise a FG=function group (FG) as further substituent which is either bound directly or via suitable bridges to the N∩L-substituent, wherein the function group is selected from the group consisting of electron conductor, hole conductor and groups which change the solubility of the complex, in particular increase the solubility in organic solvents;

"*" indicates the atom which receives the complex bond; and

"#" indicates the atom which mediates the bond with the second chemical unit;

wherein the copper (I) complex optionally
has a $\Delta E(S_1\text{-}T_1)$-value between the lowest excited singlet ($S_1$) state and the triplet ($T_1$) state below it of smaller than 2500 cm$^{-1}$;
an emission lifetime of at the most 20 μs;
an emission quantum yield of greater than 40%, and/or
a solubility in organic solvents of at least 1 g/L.

Definition of the N∩L Ligand

The singly negatively charged ligand N∩L is preferably one of the following molecules:

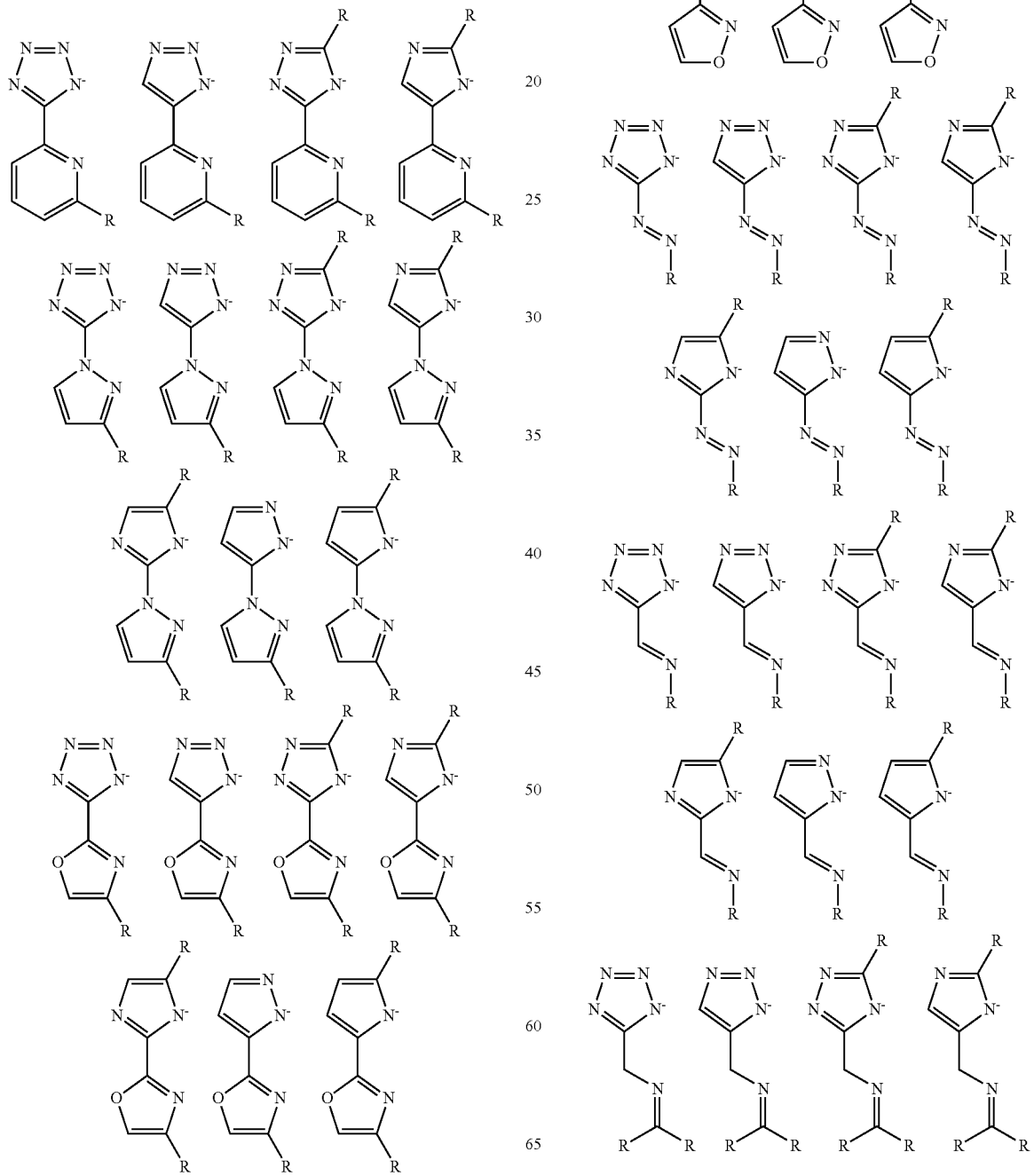

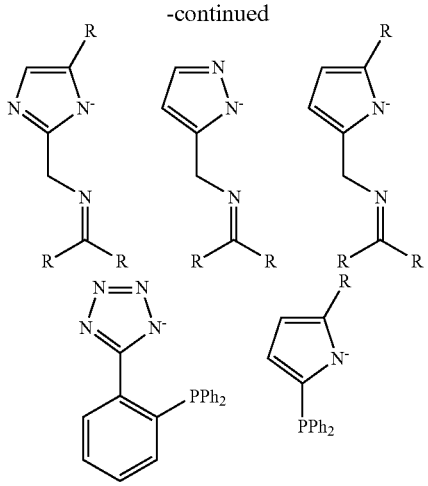

The substituent R can be an alkyl group [CH$_3$—(CH$_2$)$_n$—] (n=1-20), which can also be branched or substituted with halogens (F, Cl, Br, I) or deuterium, or an aryl group (in particular phenyl), which can be substituted with alkyl groups, halogens (F, Cl, Br, I), deuterium, silane (—SiR'3) or ether groups —OR' (R' defined as R). Likewise, R can be unsaturated groups such as alkenyl and alkinyl groups which again can be substituted with alkyl groups, halogens (F, Cl, Br, I), deuterium, silane (—SiR"$_3$) or ether groups —OR" (R" defined as R). R can yet also be a hydrogen atom or deuterium. In a preferred embodiment of the invention, the substituent R of the N∩L ligand corresponds to the sterically demanding substituent R" of formula A.

In a preferred embodiment of the invention, the ring A of the N∩L ligand corresponds to a tetrazole ring. In mononuclear, neutral complexes, compared to cationic complexes, the electronic influences of the ligands on the complex structure and the luminescence properties prevail: Compared to a neutral ligand, the anionic ligand increases the electron density at the copper(I) atom and thereby increases its HOMO, which leads to a higher sensitivity towards oxidation (T. McCormick, W. L. Jia, S. Wang, *Inorg. Chem.* 2006, 45, 147-55. *Phosphorescent Cu(I)Complexes of 2-(2'-pyridyl-benzimidazolyl)benzene: Impact of Phosphine Ancillary Ligands on Electronic and Photophysical Properties of the Cu(I)Complexes*). In order to achieve a strong coordination and thereby a rigid complex structure, which is indispensable for high quantum yields, the donor centers of the anionic ligands may induce an electron density that is as small as possible. This means for the ligand structure that the negative charge is either located at a not coordinating atom or should be delocalized by mesomerism. Known for the delocalization of a negative charge after deprotonation are tetrazoles which accordingly have high acidities with pK$_a$≈3-5. This again favors the synthesis of the complexes because a milder base can be applied and thus less side reactions occur. Instead of the model of the orbital layers the HSAB concept according to Pearson can also be used, according to which the coordinating center of the anionic ligand should be as soft as possible, i.e. the negative charge should be delocalized in order to develop a strong coordination to the soft Cu(I) atom.

The N∩L ligand can be substituted with at least one function group FG at suitable points. This way, direct C$_{FG}$—C$_{NN}$ bonds can be formed, wherein C$_{NN}$ is a C atom of the N∩L ligand and C$_{FG}$ is a C atom of the function group. If the tethering atom is a nitrogen atom, N$_{FG}$—C$_{NN}$ bonds will result, wherein N$_{FG}$ stands for the nitrogen atom. On the other hand, the function group can be bound to the N∩L ligand via a bridge, wherein the bridge is e.g. ether, thioether, ester, amide, methylene, silane, ethylene, ethine bridges. Thereby, for example, the following functions can result as bridges: C$_{FG}$—O—C$_{NN}$, C$_{FG}$—S—C$_{NN}$, —C$_{FG}$—C(O)—O—C$_{NN}$—, C$_{FG}$—C(O)—NH—C$_{NN}$—, C$_{FG}$—CH$_2$—C$_{NN}$, C$_{FG}$—SiR'$_2$—C$_{NN}$, C$_{FG}$—CH=CH—C$_{NN}$, C$_{FG}$—C≡C—C$_{NN}$, N$_{FG}$—CH$_2$—C$_{NN}$.

The method for connecting the function group to the N∩L ligand, either directly of via a bridge, are known to the person skilled in the art (Suzuki-, Still-, Heck-, Sonogashira-, Kumuda-, Ullmann-, Buchwald-Hartwig-coupling as well as their variants; (thio)etherification, esterification, nucleophilic and electrophilic substitutions at the sp$^3$-carbon atom or aromatic compounds, etc.). For example, the ligand (4,4'-bis(5-(hexylthio)-2,2'-bithiene-5'-yl)-2,2'-bipyridine) described in the literature illustrates the possibility of the connection of an electrophilic substituent to a bpy ligand via a Stille coupling (C.-Y. Chen, M. Wang, J.-Y. Li, N. Pootrakulchote, L. Alibabaei, C.-h. Ngoc-le, J.-D. Decoppet, J.-H. Tsai, C. Grätzel, C.-G. Wu, S. M. Zakeeruddin, M. Grätzel, *ACS Nano* 2009, 3, 3103).

Another possibility for synthesizing substituted N∩L ligands is the coupling of two N and L rings, which are already substituted with the group R as well as the function group FG. The resulting N∩L ligands can thus also be substituted asymmetrical. The methods and relevant literature are summarized in the review article of G. Chelucci (G. Chelucci, R. P. Thummel, *Chem. Rev.* 2002, 102, 3129).

In a particular embodiment, the group R can also be a substituent that conducts electrons, conducts holes or increases the solubility.

Definition of the L-B-L Ligand

The neutral L-B-L ligand can be one of the molecules shown below:

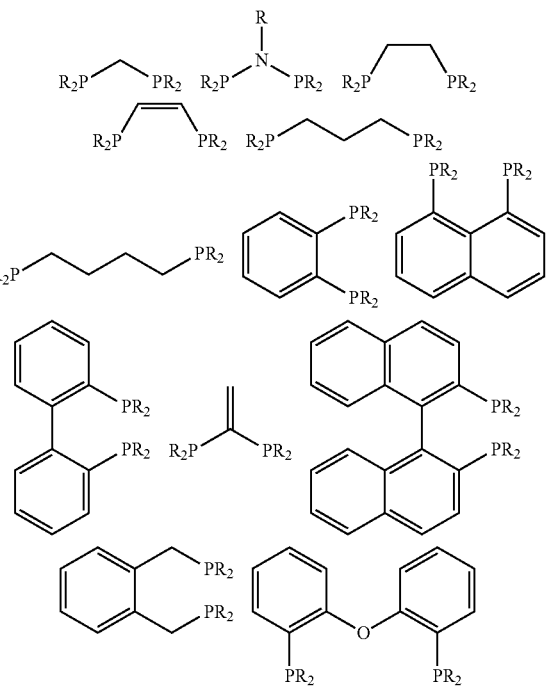

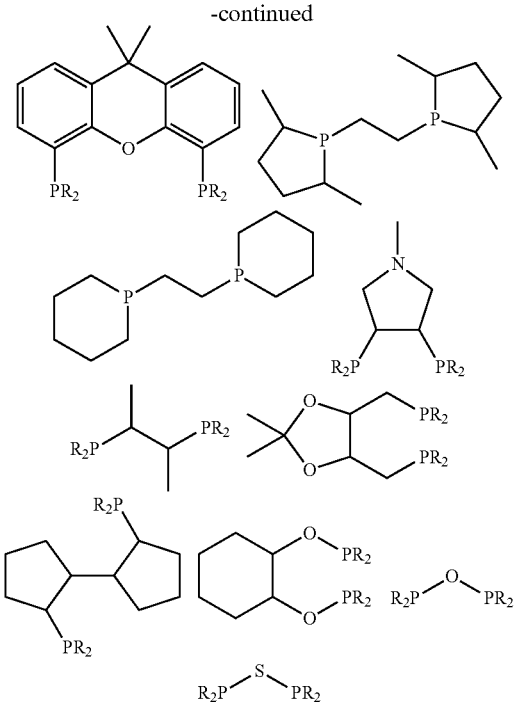

The substituent R is an alkyl group [CH$_3$—(CH$_2$)$_n$—] (n=0-20), which can also be branched or substituted with halogens (F, Cl, Br, I) or deuterium, or an aryl group (in particular phenyl), which can be substituted with alkyl groups, halogens (F, Cl, Br, I), or deuterium, silane (—SiR'$_3$) or ether groups —OR' (R' defined as R). Likewise, R can be unsaturated groups such as alkenyl and alkinyl groups which again can be substituted with alkyl groups, halogens (F, Cl, Br, I), or deuterium, silane (—SiR''$_3$) or ether groups —OR'' (R'' defined as R).

Definition of the Function Groups FG:

The function groups (FG) can be attached once or multiple times to the N∩L ligand. Identical of different function groups can be used. The function groups can also be present in a symmetrical or an unsymmetrical way. Due to synthetic reasons, a double substitution of identical function groups is usually advantageous.

Electron Conductor

Since the electron conductor materials are exclusively aromatic compounds, a substitution is possible using conventional coupling reactions. As coupling reactions, for example Suzuki-, Still-, Heck-, Sonogashira-, Kumuda-, Ullmann-, Buchwald-Hartwig-couplings as well as their variants can be used.

A N∩L ligand or L-B-L ligand substituted with a halogenide (Cl, Br, I), in particular Br or I, is reacted with a corresponding electron conducting material substituted with a suitable leaving group. Favorable is the performance of a Suzuki-coupling using the corresponding arylboronic acids and esters as well as a Buchwald-Hartwig-coupling for generating aryl-N-bonds. Depending on the function groups, further common attachment reactions can also be used, e.g. via a bridge between function group FG and N∩L ligand. In the presence of —OH groups, esterification and etherification may be used, with —NH$_2$ groups imine and amide formation, with —COOH groups esterification. The substitution pattern of the N∩L must be adapted accordingly (see above under "N∩L Ligand"). Methods for attaching the function groups FG are known to a person skilled in the art.

As an electron transport substituent, the following groups can for example be used, (attachment takes place at the position marked with an #):

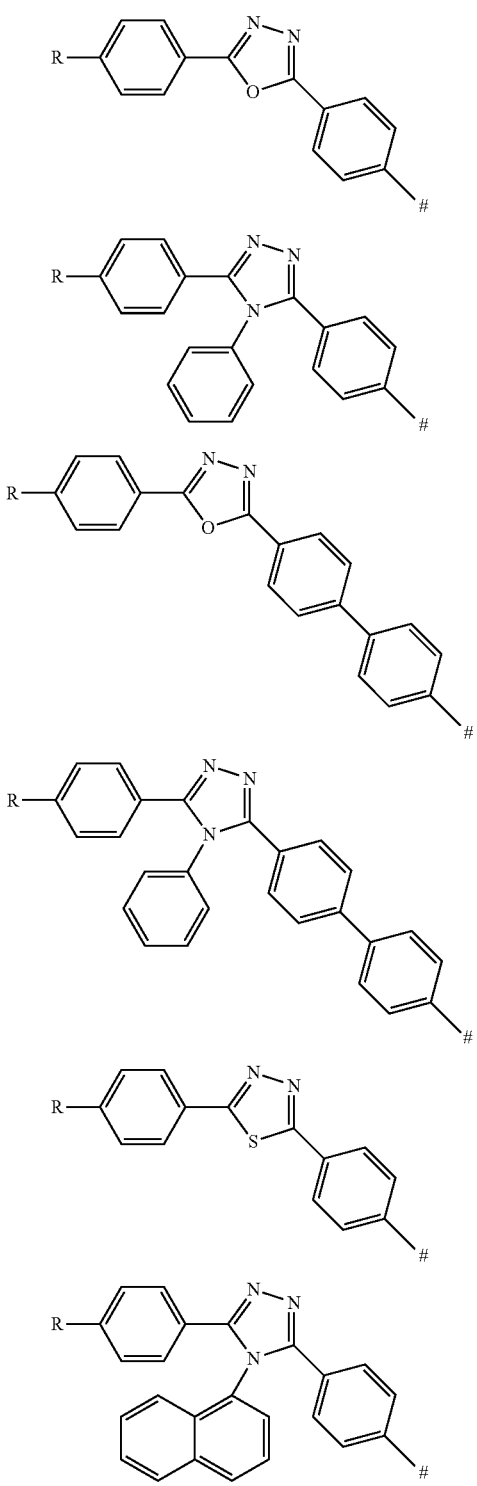

-continued

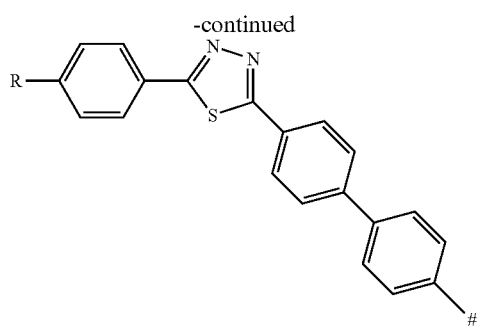

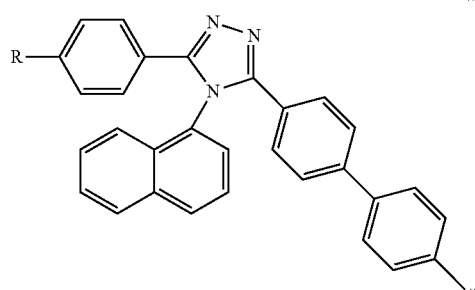

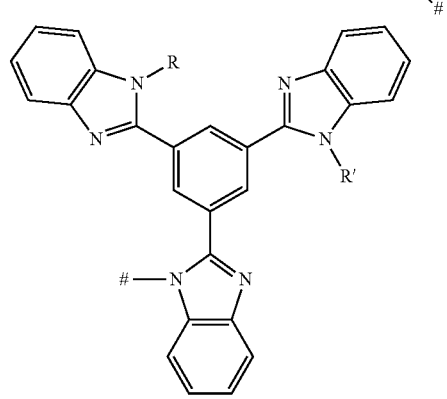

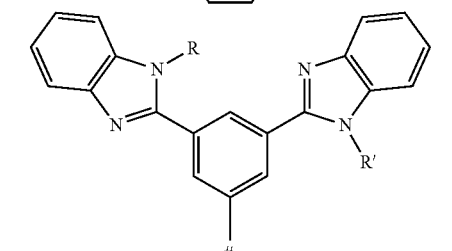

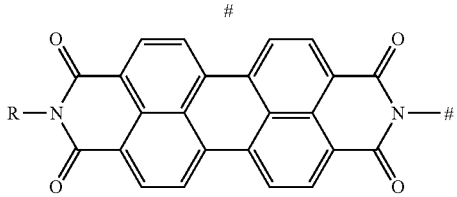

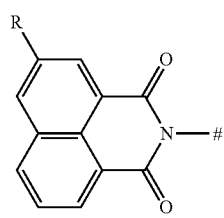

The substituents R and R' are an alkyl group [CH$_3$—(CH$_2$)$_n$—] (n=0-20), that can also be branched or substituted with halogens (F, Cl, Br, I) or deuterium or an aryl group (in particular phenyl), that can be substituted with alkyl groups, halogens (F, Cl, Br, I), or deuterium, silane (—SiR'''$_3$) or ether groups —OR''' (R''' defined like R; the substituents used herein do not necessarily correspond to the substituents R, R', R'' of formula A). Likewise, R can be an unsaturated group such as alkenyl and alkinyl groups, which again can be substituted with alkyl groups, halogens (F, Cl, Br, I), or deuterium, silane- (—SiR''$_3$) or ether groups —OR'' (R'' defined as R).

Hole Conductors

For the hole conductors, generally the analogous applies as for the electron conductors. The attachment of the hole conductor to the N∩L ligand can also most conveniently be realized through palladium-catalyzed coupling reactions; further ways of attachments, also via a bridge, are possible.

As hole transport substituents, the following groups can, for example, be used (attachment take place at the position marked with an #):

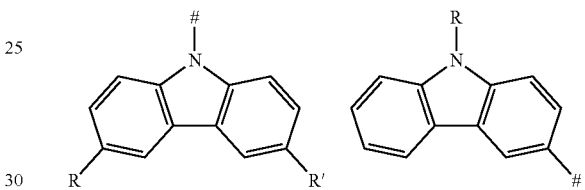

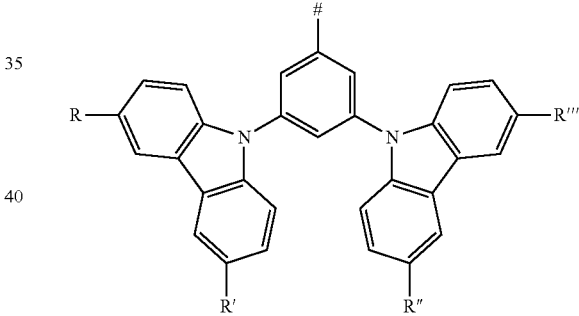

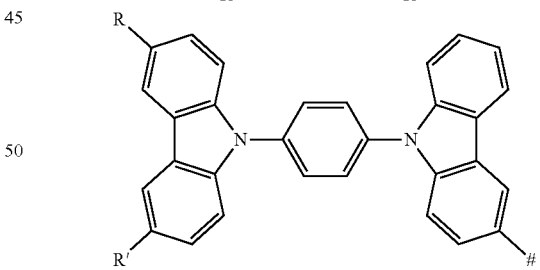

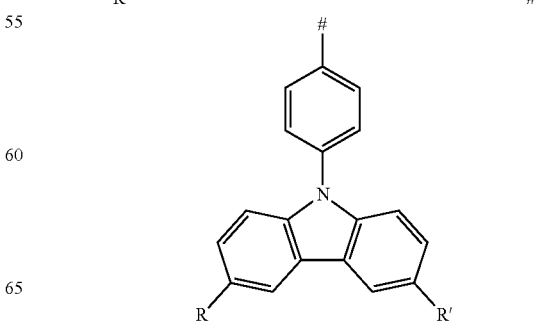

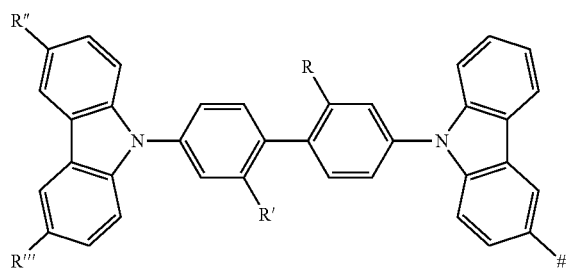
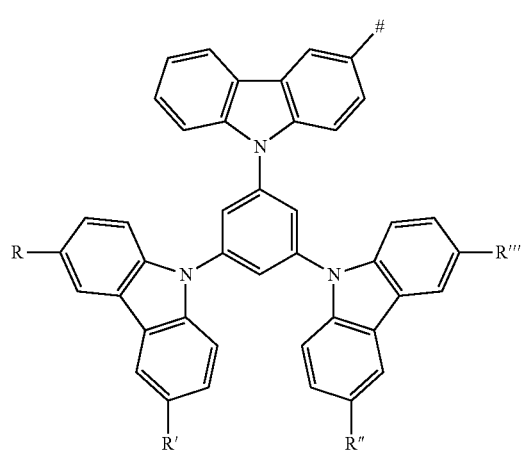
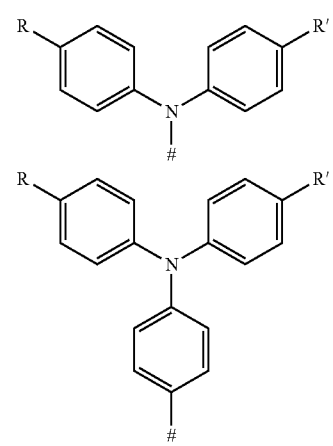
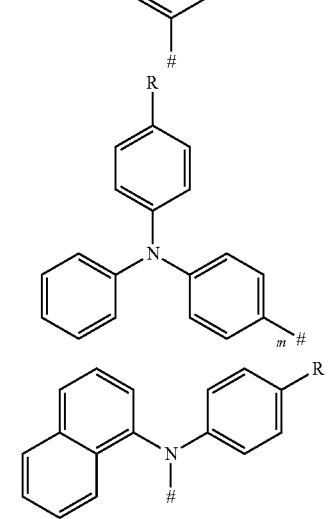
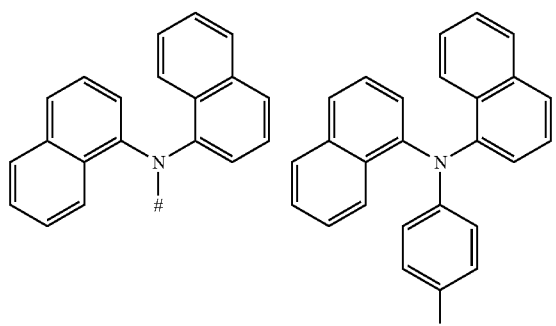
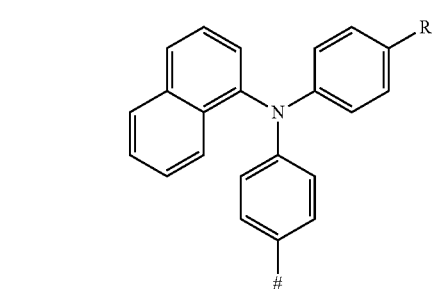
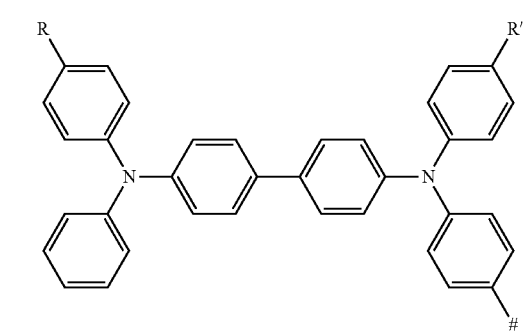
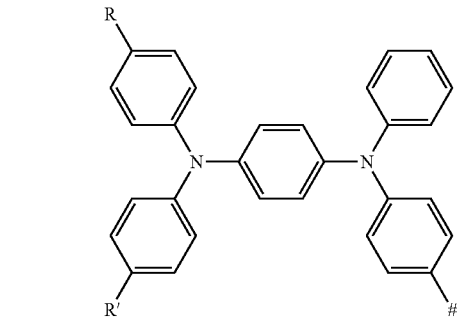
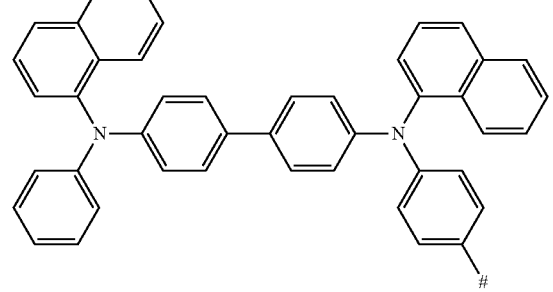

-continued

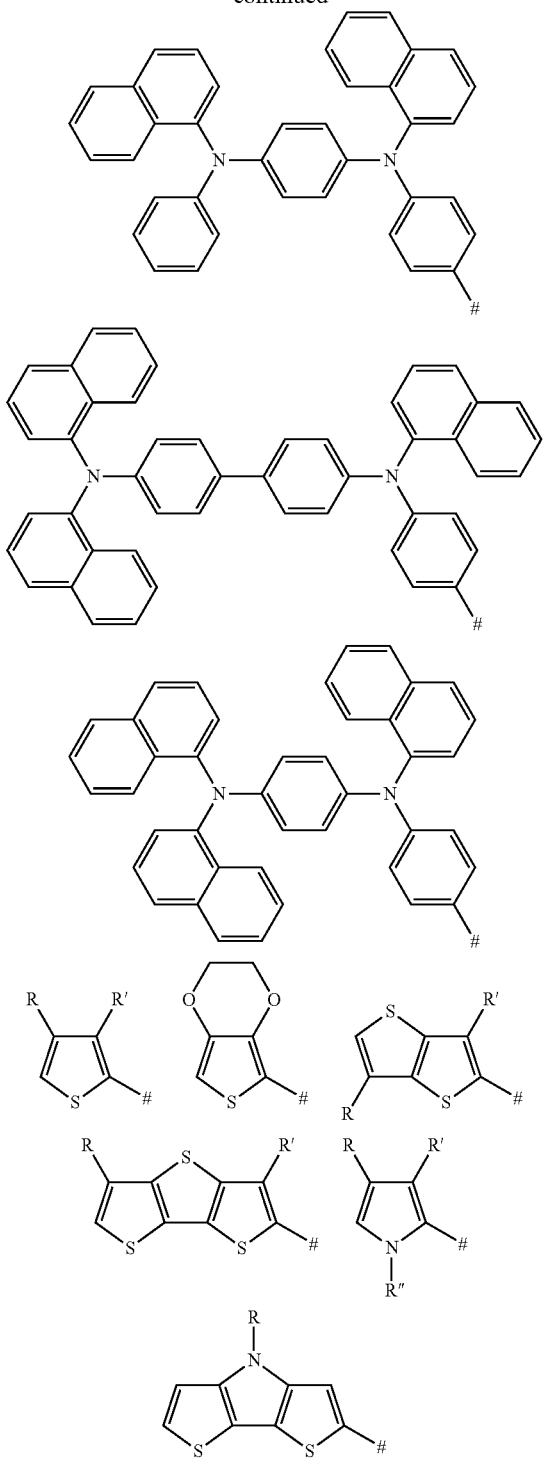

The substituents R, R'' and R''' are an alkyl group [CH$_3$—(CH$_2$)$_n$—] (n=0-20) that can also be branched or substituted with halogens (F, Cl, Br, I) or deuterium, or an aryl group (in particular phenyl), that can be substituted with alkyl groups, halogens (F, Cl, Br, I), or deuterium, silane (—SiR''''$_3$) or ether groups —OR'''' (R'''' defined like R; the substituents used herein do not necessarily correspond to the substituents R, R', R'' of formula A). Likewise, R can be an unsaturated group such as alkenyl and alkinyl groups, which again can be substituted with alkyl groups, halogens (F, Cl, Br, I), or deuterium, silane- (—SiR''$_3$) or ether groups —OR'' (R'' defined as R).

Solubility

When manufacturing optoelectronic devices using wet-chemical processes, it is advantageous to specifically regulate the solubility. Thereby, the complete or partial dissolution of a layer already deposited can be avoided. By introducing special substituents, the solubility characteristics can be strongly influenced. Thereby, it is possible to use orthogonal solvents that dissolve only the substance of the instant manufacturing step, but not the substances of the layer(s) below.

Solubility in Nonpolar Media

Nonpolar function groups FG increase the solubility in nonpolar solvents and decrease the solubility in polar solvents. Nonpolar groups are, e.g. alkyl groups [CH$_3$—(CH$_2$)$_n$—] (n=1-30), also branched, substituted alkyl groups, e.g. with halogens. Particular notice deserve: partially or perfluorinated alkyl groups as well as perfluorinated oligo- and polyethers, e.g. [—(CF$_2$)$_2$—O]$_n$— and (—CF$_2$—O)$_n$— (n=2-500). Further nonpolar groups are: ether —OR, thioether —SR, differently substituted silanes R$_3$Si— (R=alkyl or aryl), siloxanes R$_3$Si—O—, oligosiloxanes R'(—R$_2$Si—O)$_n$— (R'=R, n=2-20), polysiloxanes R'(—R$_2$Si—O)$_n$— (n>20); oligo/polyphosphazenes R'(—R$_2$P=N—)$_n$— (n=1-200).

Solubility in Polar Media

Polar function groups increase the solubility in polar media. These can be:

Alcohol groups: —OH

Thioalcohols —SH

Carboxylic acid, phosphonic acid, sulfonic acid groups as well as their salts and esters (R=H, alkyl, aryl, halogen; cations: alkali metals, ammonium salts): —COOH, —P(O)(OH)$_2$, —P(S)(OH)$_2$, —S(O)(OH)$_2$, —COOR, —P(O)(OR)$_2$, —P(S)(OR)$_2$, —S(O)(OR)$_2$, —CONHR, —P(O)(NR$_2$)$_2$, —P(S)(NR$_2$)$_2$, —S(O)(NR$_2$)$_2$ Sulfoxides: —S(O)R, —S(O)$_2$R Carbonyl groups: —C(O)R Amines: —NH$_2$, NR$_2$, —N(CH$_2$CH$_2$OH)$_2$, Hydroxylamines =NOR Oligoesters, —O(CH$_2$O)$_n$, —O(CH$_2$CH$_2$O—)$_n$ (n=2-200)

Positively charged substituents: e.g. ammonium salts —N$^+$R$_3$X$^-$, phosphonium salts —P$^+$R$_3$X$^-$ Negatively charged substituents: e.g. borate —(BR$_3$)$^-$, aluminate —(AlR$_3$)$^-$ (the anion can be an alkali metal or ammonium ion).

In order to avoid the presence of freely movable ions, positively and negatively charged substituents can be united in a function group FG.

The copper(I) complexes of formula A can be applied according to the invention as emitters in an emitter layer of a light emitting optoelectronic component. The optoelectronic components are preferably the following: organic light emitting components (OLEDs), light emitting electrochemical cells, OLED-sensors (in particular in gas and vapor sensors which are not hermetically screened from the outside), organic solar cells, organic field-effect transistors, organic lasers and down-conversion elements.

According to the invention, the copper(I) complexes of formula A can also be applied as absorber materials in an absorber layer of an optoelectronic component.

The term "optoelectronic components" refers in particular to:

organic light emitting components (organic light emitting diodes, OLEDs), light emitting electrochemical cells (LECs, LEECs), OLED-sensors, in particular in gas and vapor sensors, which are not hermetically screened from the outside,
organic solar cells (OSCs, organic photovoltaics, OPVs),
organic field-effect transistors, and
organic lasers.

In one embodiment of the invention, the ratio of the copper (I) complex in the emitter layer or absorber layer in such an optoelectronic component is 100%. In an alternative embodiment, the ratio of the copper(I) complex in the emitter layer or absorber layer is 1% to 99%.

Preferably, the concentration of the copper(I) complex as emitter in optical light emitting components, particularly in OLEDs, is between 4% and 50%.

The present invention also pertains to optoelectronic components which comprise a copper(I) complex as described herein. The optoelectronic component can be implemented as an organic light emitting component, an organic diode, an organic solar cell, an organic transistor, as an organic light emitting diode, a light emitting electrochemical cell, an organic field-effect transistor and as an organic laser.

Accordingly, the invention relates in another aspect to a method for the preparation of an optoelectronic device, in particular wherein the preparation is carried out by wet-chemical means and the method comprises the following steps:

Depositing a first emitter complex dissolved in a first solvent onto a carrier, and depositing a second emitter complex dissolved in a second solvent onto the carrier; wherein the first emitter complex is not soluble in the second solvent, and the second emitter complex is not soluble in the first solvent; and wherein the first emitter complex and/or the second emitter complex is a copper(I) complex according to the invention. The method can further comprise the following step: Depositing a third emitter complex dissolved in a first solvent or in a third solvent onto the carrier, wherein the third complex is a copper(I) complex according to the invention. First and second solvent are not identical.

In a preferred embodiment, the optoelectronic device is a white-light OLED, wherein the first emitter complex is a red-light emitter, the second emitter complex is a green-light emitter and the third emitter complex is a blue-light emitter.

Another aspect of the invention relates to a method for altering the emission and/or absorption properties of an electronic component. Thereby a copper(I) complex according to the invention is introduced into a matrix material for conducting electrons or holes into an optoelectronic component.

Another aspect of the invention relates to the use of a copper(I) complex according to the invention, particularly in an optoelectronic component, for conversion of UV radiation or of blue light to visible light, especially to green, yellow or red light (down-conversion).

EXAMPLES

Synthesis of Cu(I) Complexes

By using the ligands shown above, the corresponding neutral Cu(N∩L)(L-B-L) complexes are produced:

Example 1

The appropriate N∩L ligand (1.00 mmol, 1.00 eq.), [Cu(CH$_3$CN)$_4$]PF$_6$ (10) (1.00 mmol, 1.00 eq.) and the L-B-L ligand (1.00 mmol, 1.00 eq.) were dissolved in 10 mL solvent mixture consisting of dichloromethane:ethanol=3:1 under nitrogen atmosphere and stirred for 4 h. The complex was purified by precipitation in diethyl ether, filtered, washed with diethyl ether and dried.

The complex obtained above (0.05 mmol, 1.00 eq.) and KOH (7.75 mmol, 15.0 eq.) were dissolved in 5 mL methanol under nitrogen atmosphere and stirred for 6 h. Subsequently, the solvent was removed in vacuo, the residue extracted with DCM and filtered. After removal of the solvent the complex was obtained as a white powder.

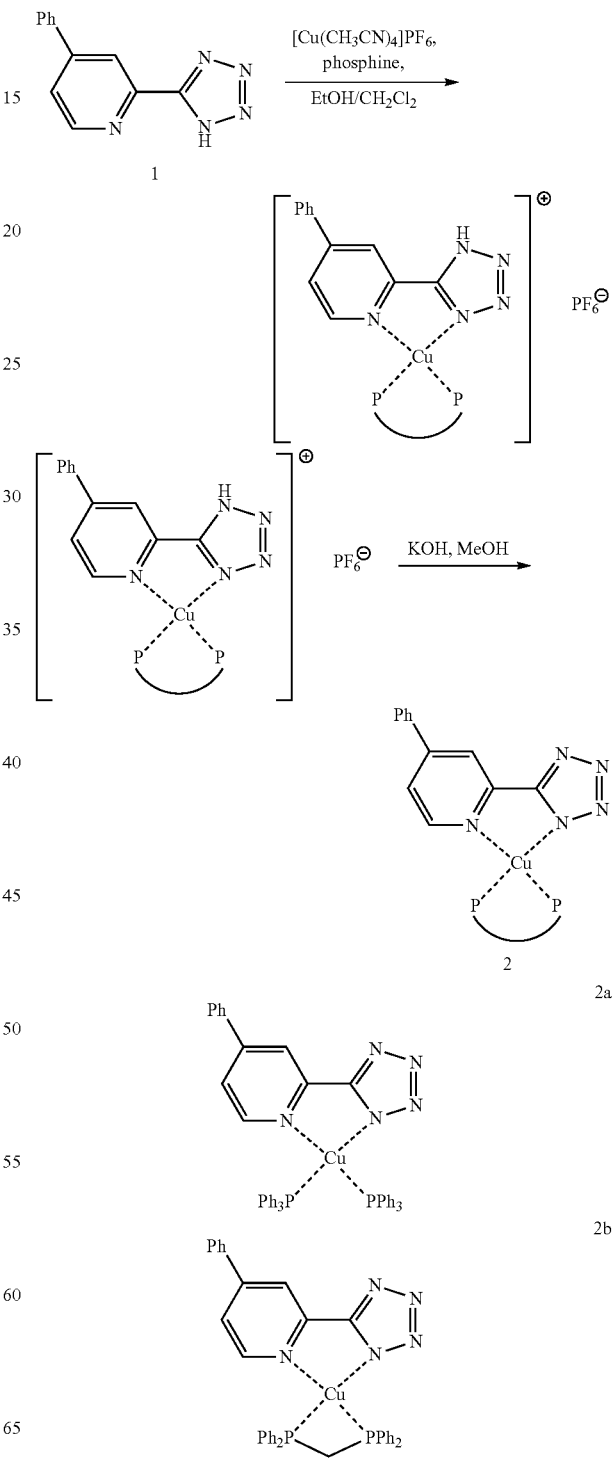

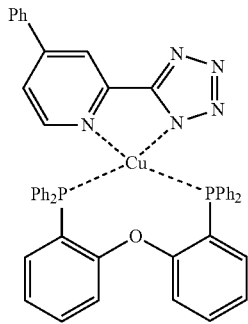

2c

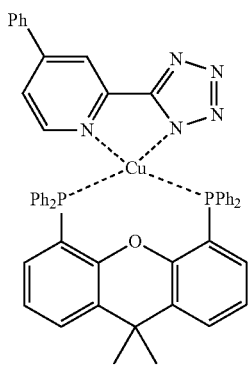

2d

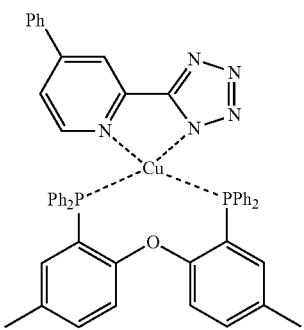

2e

2c: L-B-L=Bis(diphenylphosphine)diphenylether

Characterization:
Elemental analysis: $C_{48}H_{36}CuN_5OP_2$ (823.17): calc. C, 69.94; H 4.40; N 8.50; found C 69.41; H 4.47; N 8.00.

MS (FAB), m/z (%): 1423 (3) [LCu$_2$(P^P)$_2$], 1139 (1) [Cu(P^P)$_2$], 888 (1) [LCu$_2$P^P], 860 (6) [LCu$_2$P^P—N$_2$], 823 (7) [LCuP^P], 767 (5) [LCuP^P—N$_4$], 692 (1) [LCuP^P—N$_4$-Ph], 601 (100) [CuP^P], L: tetrazole ligand, P^P: phosphine ligand. The crystal structure of 2c is shown in FIG. 3.

The emission spectrum of 2c at 298 K is shown in FIG. 6.
The emission spectrum of 2c at 77 K is shown in FIG. 6.
The emission quantum yield of 2c is 38% (measured with Hamamatsu C9920-02G).
The emission lifetime of 2c is 2.8 μs (Horiba Fluoromax 4 with TCSPC).
The $\Delta E(S_1\text{-}T_1)$-value of 2c is 766 cm$^{-1}$ (determined by measuring the temperature dependency of the fluorescence and the phosphorescence intensity)

2d: L-B-L=(9,9-Dimethyl-9H-xanthene-4,5-diyl)bis(diphenylphosphine)

Characterization:
Elemental analysis: $C_{51}H_{40}CuN_5OP_2$ (863.20): calc. C 70.86, H 4.66, N 8.10; found C 69.59, H 4.77, N 7.61.

MS (FAB), m/z (%): 1790 (1) [L$_2$Cu$_3$(P^P)$_2$], 1505 (18) [LCu$_2$(P^P)$_2$], 1220 (1) [Cu$_2$(P^P)$_2$], 957 (2), 926 (2) [LCu$_2$P^P], 863 (2) [LCuP^P], 808 (7) [LCuP^PN$_4$], 730 (2) [LCuP^P—N$_4$-Ph], 641 (100) [CuP^P], L: tetrazole ligand, P^P: phosphine ligand.

The crystal structure of 2d is shown in FIG. 4.
The emission spectrum of 2d at 298 K is shown in FIG. 7.
The emission spectrum of 2d at 77 K is shown in FIG. 7.
The emission quantum yield of 2d is 80% (measured with Hamamatsu C9920-02G).
The emission lifetime of 2d is 0.8 μs (Horiba Fluoromax 4 with TCSPC).
The $\Delta E(S_1\text{-}T_1)$ value of 2d is 464 cm$^{-1}$ (determined by measuring the temperature dependency of the fluorescence and the phosphorescence intensity)

2e: L-B-L=(Oxybis(3-methyl-6,1-phenylene))bis(diphenylphosphine)

Characterization:
Elemental analysis: $C_{50}H_{40}CuN_5OP_2$ (851.20): calc. C 70.22, H 5.10, N 7.87 (+ 0.5× Et$_2$O.; found C 69.31, H 4.96, N 7.07.

The emission spectrum of 2e at 298 K is shown in FIG. 8.
The emission spectrum of 2e at 77 K is shown in FIG. 8.
The emission quantum yield of 2e is 92% (measured with Hamamatsu C9920-02G).
The emission lifetime of 2e is 1.1 μs (Horiba Fluoromax 4 with TCSPC).
The $\Delta E(S_1\text{-}T_1)$ value of 2e is 453 cm$^{-1}$ (determined by measuring the temperature dependency of the fluorescence and the phosphorescence intensity)

Example 2

The N∩L ligand (1.00 mmol, 1.00 eq.) was dissolved in 10 mL dichloromethane under nitrogen atmosphere, an equimolar amount of base added and stirred for 1 hour. Then an equimolar amount of Cu(CH$_3$CN)$_4$]BF$_4$ was added, stirred for 1 hour, an equimolar amount of the appropriate L-B-L ligand added and stirred over night. The complex was purified by precipitation in diethyl ether, filtered, washed with diethyl ether and dried.

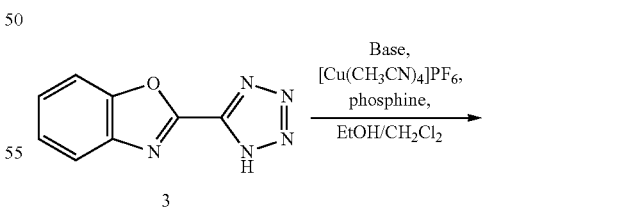

3

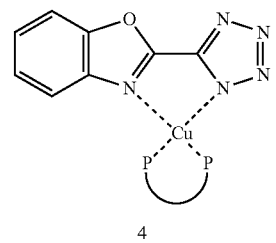

4

-continued

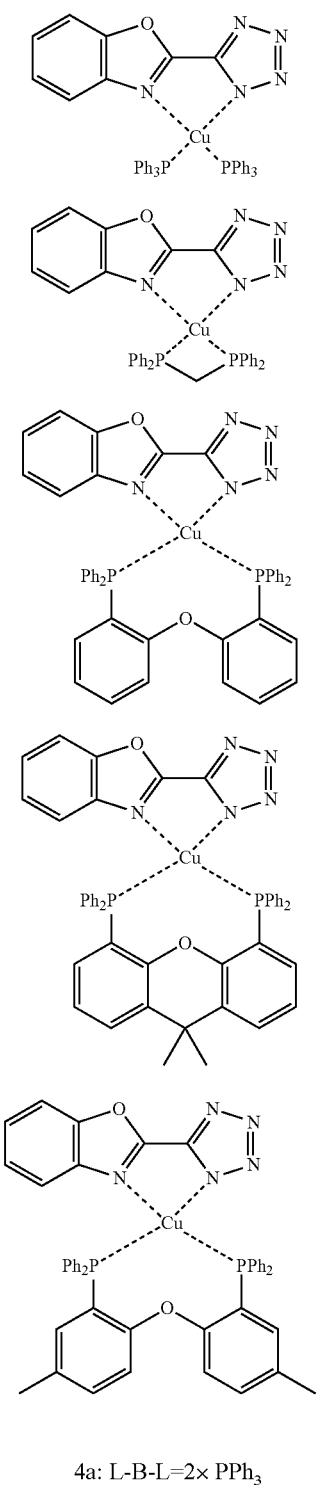

4a: L-B-L=2× PPh$_3$

Characterization:
The emission lifetime of 4a is 0.8 μs (Horiba Fluoromax 4 with TCSPC).

4c: L-B-L=Bis(diphenylphosphine)diphenylether

Characterization:
The emission spectrum of 4c at 298 K is shown in FIG. 9.
The emission spectrum of 4c at 77 K is shown in FIG. 9.

The emission quantum yield of 4c is 65% (measured with Hamamatsu C9920-02G).

The emission lifetime of 4c is 1.0 μs (Horiba Fluoromax 4 with TCSPC).

The $\Delta E(S_1\text{-}T_1)$ value of 4c is 169 cm$^{-1}$ (determined by measuring the temperature dependency of the fluorescence and the phosphorescence intensity)

4e: L-B-L=(Oxybis(3-methyl-6,1-phenylene))bis(diphenylphosphine)

Characterization:
MS (FAB), m/z (%): 1691 (1) [L$_2$Cu$_3$(P^P)$_2$], 1534 (1), 1446 (3) [LCu$_2$(P^P)$_2$], 1284 (2) [LCu(P^P)$_2$—N$_4$—(CH$_3$)$_3$], 853 (6) [LCuP^P—N$_2$], 816 (2) [LCuP^P], 759 (4) [LCuP^P—N$_4$], 629 (100) [CuP^P], L: tetrazole ligand, P^P: phosphine ligand.

Example 3

The synthesis was carried out as mentioned in example 2.

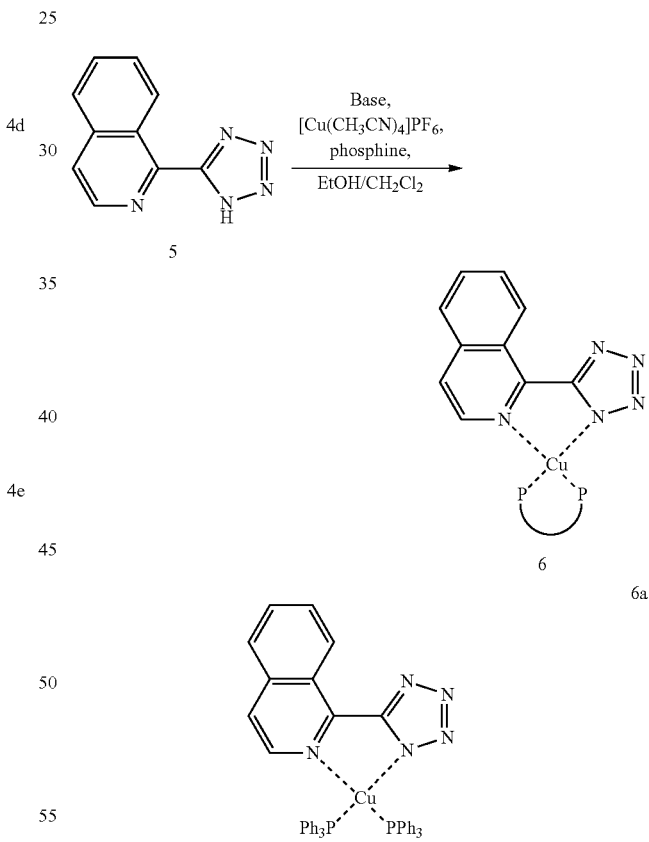

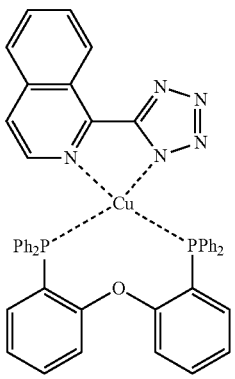

6c

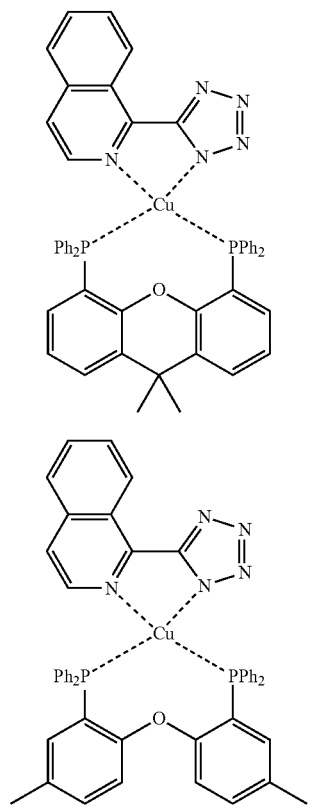

6d

6c: L-B-L=Bis(diphenylphosphin)diphenylether

Characterization:

MS (FAB), m/z (%): 2195 (1) [L$_2$Cu$_3$(P^P)$_3$], 1917 (1) [L$_3$Cu$_4$(P^P)$_2$], 1660 (1) [L$_2$Cu$_3$(P^P)$_2$], 1400 (10) [LCu$_2$(P^P)$_2$], 1140 (2) [Cu(P^P)$_2$], 860 (5) [LCu$_2$(P^P)], 798 (4) [LCuP^P], 741 (6) [LCuP^P—N$_4$], 602 (100) [CuP^P].

The emission spectrum of 6c at 298 K is shown in FIG. 10.

The emission quantum yield of 6c is 20% (measured with Hamamatsu C9920-02G).

The emission lifetime of 6c is 0.7 μs (Horiba Fluoromax 4 with TCSPC).

6e: L-B-L=(Oxybis(3-methyl-6,1-phenylene))bis(diphenylphosphine)

Characterization:

MS (FAB), m/z (%): 2278 (1) [L$_4$Cu$_6$(P^P)$_2$—CH$_3$], 1713 (2) [L$_2$Cu$_3$(P^P)$_2$], 1455 (12) [LCu$_2$(P^P)$_2$], 1196 (1) [Cu(P^P)$_2$], 889 (7) [LCu$_2$(P^P)], 825 (2) [LCuP^P], 769 (3) [LCuP^P—N$_4$], 739 (2) [LCuP^P—N$_4$—(CH$_3$)$_2$], 692 (2) [Cu$_2$P^P], 629 (100) [CuP^P], L: tetrazole ligand, P^P: phosphine ligand.

The emission spectrum of 6e at 298 K is shown in FIG. 11.

Example 4

The synthesis was carried out as mentioned in example 1.

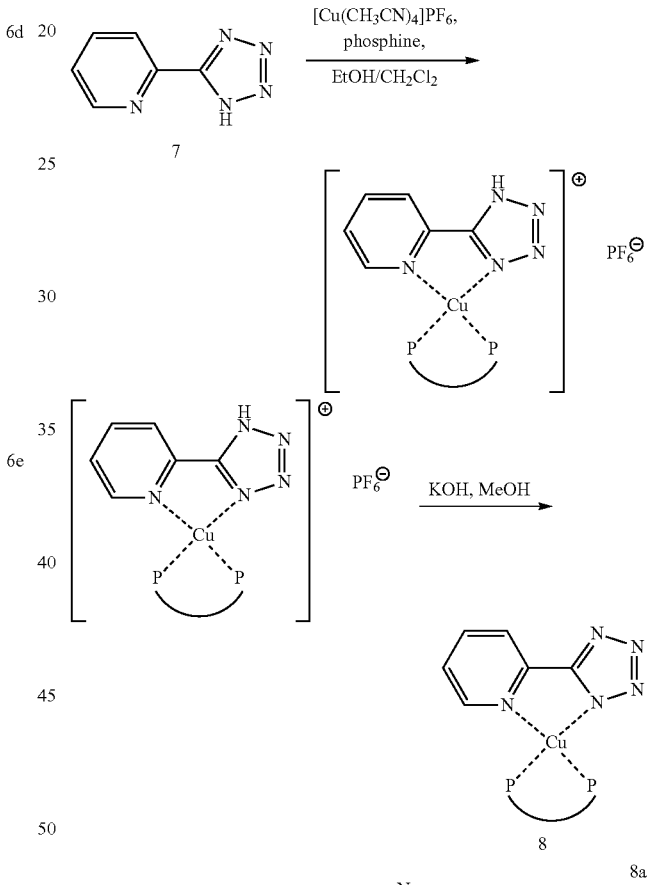

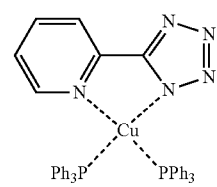

8a

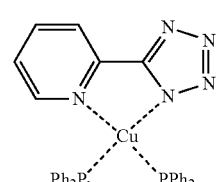

8b

-continued

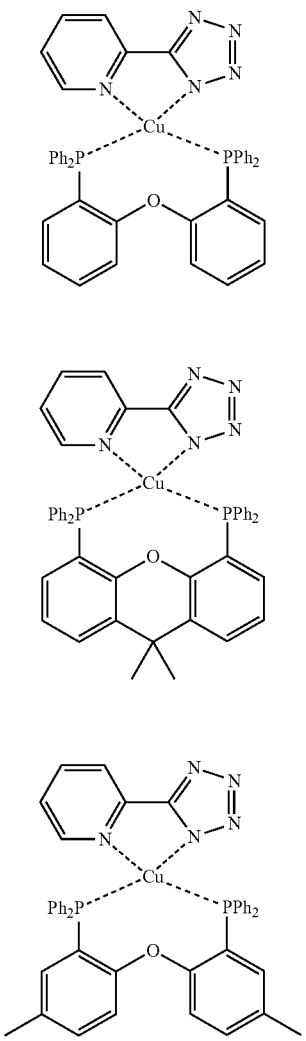

8a: L-B-L=2× PPh3

Characterization:
The crystal structure of 8a is shown in FIG. 5.
The emission quantum yield of 8a is 40% (measured with Hamamatsu C9920-02G).

8c: L-B-L=Bis(diphenylphosphine)diphenylether

Characterization:
Elemental analysis: $C_{42}H_{32}CuN_5OP_2$ (747.14): calc. C 67.42, H 4.31, N 9.36; found C 66.84, H 4.40, N 9.16
The emission spectrum of 8c at 298 K is shown in FIG. 12.
The emission spectrum of 8c at 77 K is shown in FIG. 12.
The emission quantum yield of 8c is 62% (measured with Hamamatsu C9920-02G).
The emission lifetime of 8c is 0.7 μs (Horiba Fluoromax 4 with TCSPC).
The $\Delta E(S_1\text{-}T_1)$ value of 8c is 1306 cm$^{-1}$ (determined by measuring the temperature dependency of the fluorescence and the phosphorescence intensity)

8d: L-B-L=(9,9-Dimethyl-9H-xanthene-4,5-diyl)bis(diphenylphosphine)

Characterization:
Elemental analysis: $C_{45}H_{36}CuN_5OP_2$ (787.17): calc. C 63.27, H 4.39, N 8.02 (+ 1× $CH_2Cl_2$).
found C 64.83, H 4.53, N 7.95
MS (FAB), m/z (%): 1640 (1) [$L_2Cu_3(P^{\wedge}P)_2$], 1429 (16) [$LCu_2(P^{\wedge}P)_2$], 958 (1), 850 (1) [$LCu_2P^{\wedge}P$], 787 (6) [$LCuP^{\wedge}P$], 730 (6), 641 (100) [$CuP^{\wedge}P$], L: tetrazole ligand, P^P: phosphine ligand.
The emission spectrum of 8d at 298 K is shown in FIG. 13.
The emission spectrum of 8d at 77 K is shown in FIG. 13.
The emission quantum yield of 8d is 76% (measured with Hamamatsu C9920-02G).
The emission lifetime of 8d is 0.9 μs (Horiba Fluoromax 4 with TCSPC).
The $\Delta E(S_1\text{-}T_1)$ value of 8d is 896 cm$^{-1}$ (determined by measuring the temperature dependency of the fluorescence and the phosphorescence intensity)

8e: L-B-L=(Oxybis(3-methyl-6,1-phenylene))bis(diphenylphosphine)

Characterization:
Elemental analysis: $C_{44}H_{36}CuN_5OP_2$ (775.17): calc. C 67.93, H 5.08, N 8.61 (+ 0.5× $Et_2O$); found C 67.95, H 4.97, N 8.36
MS (FAB), m/z (%): 1615 (1) [$L_2Cu_3(P^{\wedge}P)_2$], 1405 (12) [$LCu_2(P^{\wedge}P)_2$], 1196 (1) [$L_3Cu_3P^{\wedge}P$], 778 (6) [$LCuP^{\wedge}P$], 719 (6) [$LCuP^{\wedge}P-N_4$], 629 (100) [$CuP^{\wedge}P$], L: tetrazole ligand, P^P: phosphine ligand.
The emission spectrum of 8e at 298 K is shown in FIG. 14.
The emission spectrum of 8e at 77 K is shown in FIG. 14.
The emission quantum yield of 8e is 92% (measured with Hamamatsu C9920-02G).
The emission lifetime of 8e is 0.7 μs (Horiba Fluoromax 4 with TCSPC).
The $\Delta E(S_1\text{-}T_1)$ value of 8e is 1036 cm$^{-1}$ (determined by measuring the temperature dependency of the fluorescence and the phosphorescence intensity)

Example 5

The synthesis was carried out as mentioned in example 1.

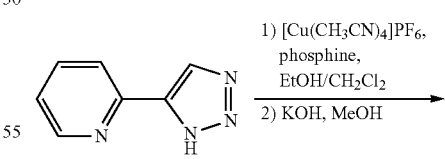

9

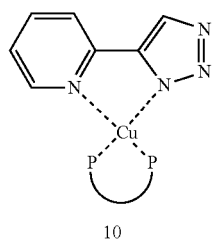

10

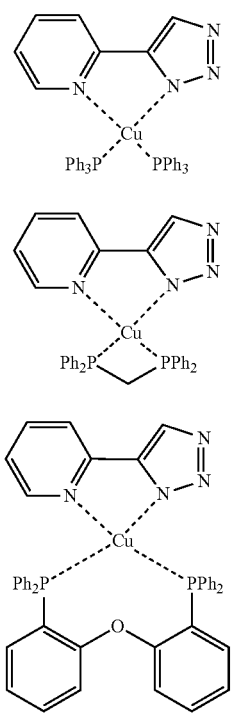
Example 6
The synthesis was carried out as mentioned in example 2.
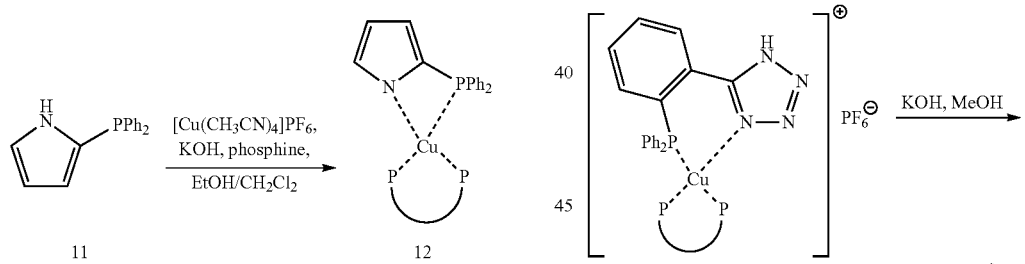
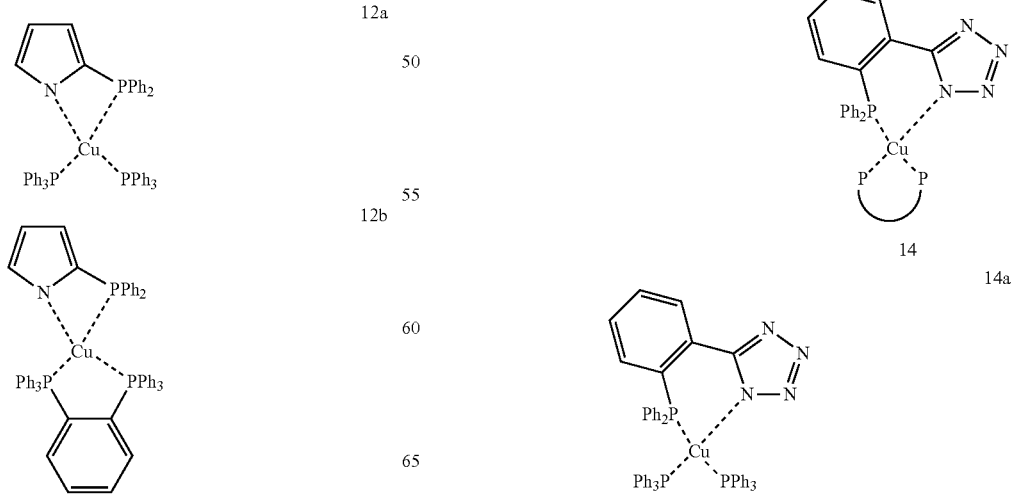
Example 7
The synthesis was carried out as mentioned in example 1.
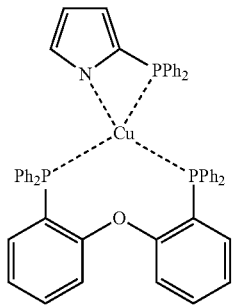
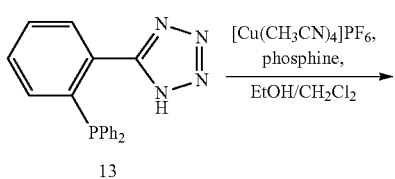
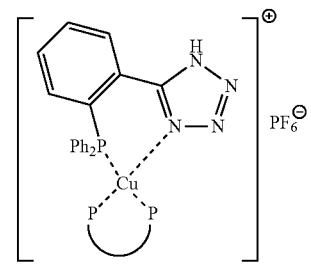

-continued

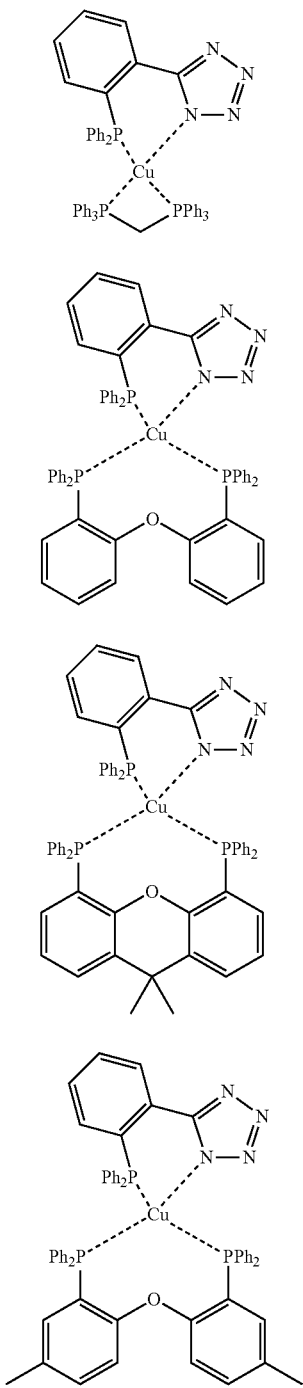

14b
14c
14d
14e

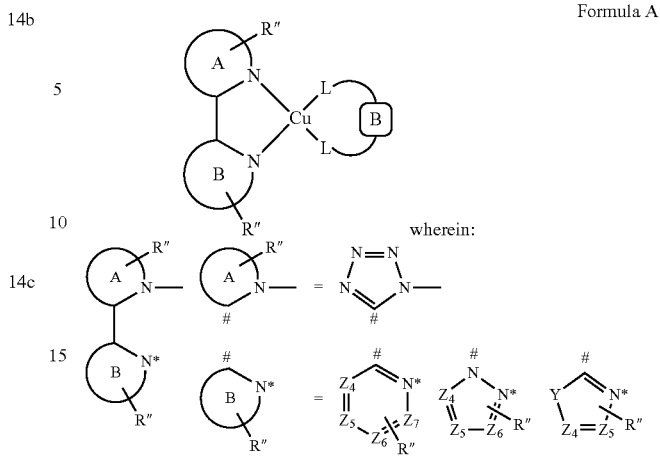

Formula A wherein:

wherein:
L-B-L is a neutral bidentate ligand, wherein:
L is a phosphinyl or arsinyl group E*(R1)(R2) which is bound to another L group via a bridge B, thereby forming a bidentate ligand;
E=P or As;
R1 and R2 are independently selected from hydrogen, halogen, deuterium, or substituents which are bound via oxygen (—OR'''), nitrogen (—NR'''$_2$) or silicon atoms (—SiR'''$_3$), alkyl, aryl, heteroaryl, alkenyl, alkinyl groups or substituted alkyl, aryl, heteroaryl and alkenyl groups with substituents selected from the group consisting of halogens, deuterium, alkyl groups (branched or cyclic), and donor and acceptor groups selected from amines, carboxylates and their esters, and CF$_3$-groups, wherein the bridge B is an alkylene or arylene group or a combination thereof, or —O—, —NR'''— or —SiR'''$_2$—;
Z4-Z7 includes N or the fragment CR;
wherein R is an organic group, selected from the group consisting of hydrogen, halogen, deuterium or substituents which are bound via oxygen (—OR'''), nitrogen (—NR'''$_2$), silicon (—SiR'''$_3$) or phosphorous atoms (PR'''$_2$), alkyl, aryl, heteroaryl, alkenyl, alkinyl groups or substituted alkyl, aryl, heteroaryl and alkenyl groups with substituents selected from halogens, deuterium, alkyl groups, and donor and acceptor groups selected from amines, carboxylates and their esters, and CF$_3$-groups;
X is CR'''$_2$ or NR''';
Y is O,S or NR''';
Z8 includes the fragment CR';
wherein R' is O*R''',N*R'''$_2$ or P*R'''$_2$, wherein the bond to the Cu atom is formed via the O*R''', N*R'''$_2$ or P*R'''$_2$ groups;
R'' is selected from an alkyl group —(CH$_2$)$_n$—CH$_3$ (n=0-20), an aryl group with 6-20 carbon atoms, alkoxy group Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:
1. A neutral mononuclear copper(I) complex for the emission of light comprising a structure according to formula A:

—O—(CH$_2$)$_n$—CH$_3$ (n=0-20), an aryloxy group or a silane group, wherein formula A comprises no, one or two groups R";

R'" is an organic group selected from the group consisting of hydrogen, halogen, deuterium, alkyl, aryl, heteroaryl, alkenyl, alkinyl groups, or substituted alkyl, aryl, heteroaryl and alkenyl groups with substituents selected from halogens, deuterium, alkyl groups, and donor and acceptor groups selected from amines, carboxylates and their esters, and CF$_3$-groups;

* indicates the atom which forms the complex bond; and # indicates the atom which forms a bond with a second chemical unit.

2. The copper(I) complex of claim 1, wherein the R1 and R2 groups form annulated rings.

3. The copper(I) complex of claim 1, wherein the alkyl group —(CH$_2$)$_n$—CH$_3$ (n =0-20) and aryl group with 6-20 carbon atoms are substituted by halogens, deuterium, alkoxy or silane groups, and lead to annulated ring systems.

4. The copper(I) complex of claim 1 further comprising a function group FG as a further substituent, wherein the function group is either bound directly or via suitable bridges to a N∩L -substituent, wherein the function group is selected from the group consisting of an electron conductor, a hole conductor and groups which increase the solubility of the complex in organic solvents.

5. The copper(I) complex of claim 1, further comprising:
a ΔE(S$_1$-T$_1$)-value between a lowest excited singlet (S$_1$) state and a triplet (T$_1$) state below the S$_1$ state, wherein the ΔE(S$_1$-T$_1$)-value is smaller than 2500 cm$^{-1}$;
an emission lifetime of at the most 20 μs;
an emission quantum yield of greater than 40%; and
a solubility in organic solvents of at least 1 g/L.

6. The copper(I) complex of claim 1, wherein the N∩L ligand is a substituted bisheteroarmatic compound which is substituted in a position ortho to the coordination point with substituents selected from alkyl [CH$_3$—(CH$_2$)$_n$—] (n =1-20) and aryl.

7. The copper(I) complex of claim 1, wherein R" is selected from the group consisting of alkyl groups —(CH$_2$)$_n$—CH$_3$ (n=0-20), aryl groups with 6-20 carbon atoms, alkoxy groups —O—(CH$_2$)$_n$—CH$_3$ (n=0-20), aryloxy groups, silane groups, and unsaturated groups comprising alkenyl and alkinyl groups which are optionally substituted with alkyl groups, halogens, deuterium, silane (—SiR""$_3$) or ether groups —OR"";
wherein R""=R"; and
wherein the alkyl and aryl groups are substituted by halogens, deuterium, alkoxy or silane groups or lead to annulated ring systems.

8. The copper(I) complex of claim 1, wherein R" increases the solubility of the copper(I) complex in organic solvents and increases a hole or an electron conductivity of the copper (I) complex.

9. The copper(I) complex of claim 1, wherein R" is an aliphatic group in an ortho position to the coordination point.

10. The copper(I) complex of claim 5, wherein the ΔE(S$_1$-T$_1$)-value is smaller than 1500 cm$^{-1}$, the emission quantum yield is greater than 60%, the emission lifetime is at most 10 μs, and the solubility in organic solvents is at least 10 g/L.

11. The copper(I) complex of claim 10, wherein the ΔE(S$_1$-T$_1$)-value is smaller than 1000 cm$^{-1}$, the emission quantum yield is greater than 70%, and the emission lifetime is at most 6 μs.

12. The copper(I) complex of claim 11, wherein the ΔE(S$_1$-T$_1$)-value is smaller than 500 cm$^{-1}$ and the emission lifetime is at the most 3 μs.

13. The copper(I) complex of claim 1, wherein the copper (I) complex is used for emission of light in an emitter layer in an optoelectronic device.

14. A method for manufacturing an optoelectronic device comprising the copper(I) complex of claim 1, wherein the manufacturing is performed using a wet-chemical process and the method comprises:
depositing a first emitter complex that is dissolved in a first solvent onto a carrier; and
depositing a second emitter complex that is dissolved in a second solvent onto the carrier;
wherein:
the first emitter complex is not soluble in the second solvent;
the second emitter complex is not soluble in the first solvent; and
wherein at least one of the first emitter complex and the second emitter complex is the copper(I) complex according to claim 1.

15. The method of claim 14, further comprising:
depositing a third emitter complex onto the carrier that is dissolved in the first solvent or a third solvent;
wherein the third emitter complex is a copper(I)complex according to claim 1.

16. The method of claim 15, wherein the optoelectronic device is a white-light organic light emitting diode (OLED), wherein:
the first emitter complex is a red-light emitter;
the second emitter complex is a green-light emitter; and
the third emitter complex is a blue-light emitter.

17. The copper(I) complex of claim 13, wherein a fraction of the copper(I) complex in the emitter layer is in the range of 2% to 100% by weight with respect to a total weight of the emitter layer.

18. The copper(I) complex of claim 17, wherein the fraction of the copper(I) complex in the emitter layer is in the range of 4% to 50% by weight with respect to the total weight of the emitter layer.

19. The copper(I) complex 17, wherein the optoelectronic device is an organic light emitting diode (OLED).

20. The copper(I) complex of claim 13, wherein the optoelectronic device is selected from the group consisting of an organic light emitting diode (OLED), a light emitting electrochemical cell (LEEC or LEC), an OLED-sensor, a gas or a vapor sensor which is not hermetically screened from the outside, an optical temperature sensor, an organic solar cell (OSC), and organic field-effect transistor, an organic laser, an organic diode, an organic photo diode and a down conversion system.

* * * * *